US009168073B2

(12) United States Patent
Aschmann et al.

(10) Patent No.: US 9,168,073 B2
(45) Date of Patent: Oct. 27, 2015

(54) SPINOUS PROCESS FIXATOR

(71) Applicant: DePuy Synthes Products, LLC, Raynham, MA (US)

(72) Inventors: Felix Aschmann, Oberdorf (CH); Benjamin Barrall, Conshohocken, PA (US); David Chow, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/835,666

(22) Filed: Mar. 15, 2013

(65) Prior Publication Data

US 2014/0277144 A1    Sep. 18, 2014

(51) Int. Cl.
*A61B 17/70* (2006.01)
(52) U.S. Cl.
CPC .................................. *A61B 17/7068* (2013.01)
(58) Field of Classification Search
CPC ........... A61B 17/7068; A61B 17/7067; A61B 17/7062
USPC .......................................... 606/246, 248, 249
See application file for complete search history.

(56) References Cited

U.S. PATENT DOCUMENTS

| 6,099,527 | A * | 8/2000 | Hochschuler et al. ........ 606/279 |
| 6,280,458 | B1 | 8/2001 | Boche et al. |
| 6,635,071 | B2 | 10/2003 | Boche et al. |
| 6,712,819 | B2 | 3/2004 | Zucherman et al. |
| 6,739,068 | B1 | 5/2004 | Rinner |
| 6,902,566 | B2 | 6/2005 | Zucherman et al. |
| 7,048,736 | B2 | 5/2006 | Robinson et al. |
| 7,081,118 | B2 | 7/2006 | Weber et al. |
| 7,189,234 | B2 | 3/2007 | Zucherman et al. |
| 7,473,268 | B2 | 1/2009 | Zucherman et al. |
| 7,569,067 | B2 | 8/2009 | Keller |
| 7,727,233 | B2 | 6/2010 | Blackwell et al. |
| 7,763,073 | B2 * | 7/2010 | Hawkins et al. ........... 623/17.11 |
| 7,922,750 | B2 | 4/2011 | Trautwein et al. |
| 8,202,299 | B2 | 6/2012 | Wang et al. |
| 8,679,161 | B2 * | 3/2014 | Malandain et al. .......... 606/249 |

(Continued)

FOREIGN PATENT DOCUMENTS

| CN | 101217917 | 7/2008 |
| DE | 10048676 | 11/2002 |

(Continued)

OTHER PUBLICATIONS

Official U.S. Office Action, dated Dec. 7, 2012, in related U.S. Appl. No. 13/058,553.

(Continued)

*Primary Examiner* — Eduardo C Robert
*Assistant Examiner* — Jacqueline Johanas
(74) *Attorney, Agent, or Firm* — Meunier Carlin & Curfman LLC

(57) ABSTRACT

The present invention is directed to an interspinous spacer assembly for implantation and/or affixation between spinous processes of adjacent superior and inferior vertebrae and associated tools and methods for stabilizing the human spine. The interspinous spacer assembly includes a spacer body, a first lateral plate, a second lateral plate and a locking mechanism extending through a channel provided in the spacer body and coupling the first and second lateral plates to the spacer body.

20 Claims, 32 Drawing Sheets

(56) References Cited

U.S. PATENT DOCUMENTS

| | | | |
|---|---|---|---|
| 2002/0029039 A1 | 3/2002 | Zucherman et al. | |
| 2003/0040746 A1 | 2/2003 | Mitchell et al. | |
| 2005/0203512 A1* | 9/2005 | Hawkins et al. | 606/61 |
| 2006/0241601 A1 | 10/2006 | Trautwein et al. | |
| 2006/0247640 A1 | 11/2006 | Blackwell et al. | |
| 2007/0179500 A1 | 8/2007 | Chin et al. | |
| 2007/0233082 A1 | 10/2007 | Chin et al. | |
| 2008/0140125 A1* | 6/2008 | Mitchell et al. | 606/279 |
| 2008/0183211 A1 | 7/2008 | Lamborne et al. | |
| 2008/0281423 A1 | 11/2008 | Sheffer et al. | |
| 2009/0062918 A1 | 3/2009 | Wang et al. | |
| 2009/0264927 A1* | 10/2009 | Ginsberg et al. | 606/246 |
| 2009/0326581 A1* | 12/2009 | Galley et al. | 606/249 |
| 2010/0036419 A1 | 2/2010 | Patel et al. | |
| 2010/0087860 A1 | 4/2010 | Chin et al. | |
| 2010/0152775 A1* | 6/2010 | Seifert et al. | 606/249 |
| 2010/0241167 A1 | 9/2010 | Taber et al. | |
| 2010/0318127 A1 | 12/2010 | Phan et al. | |
| 2011/0022090 A1 | 1/2011 | Gordon et al. | |
| 2011/0144692 A1* | 6/2011 | Saladin et al. | 606/249 |
| 2011/0172711 A1* | 7/2011 | Kirschman | 606/252 |
| 2011/0190819 A1 | 8/2011 | Trautwein et al. | |
| 2011/0224740 A1 | 9/2011 | Smisson, III et al. | |
| 2011/0319936 A1* | 12/2011 | Gordon et al. | 606/248 |
| 2012/0089184 A1* | 4/2012 | Yeh | 606/248 |
| 2012/0109203 A1* | 5/2012 | Dryer et al. | 606/249 |
| 2012/0221051 A1* | 8/2012 | Robinson | 606/249 |
| 2012/0239089 A1* | 9/2012 | Druma et al. | 606/249 |
| 2012/0323276 A1* | 12/2012 | Okamoto | 606/249 |
| 2013/0158604 A1* | 6/2013 | Okamoto | 606/249 |
| 2013/0184752 A1* | 7/2013 | Binder | 606/248 |
| 2013/0331890 A1* | 12/2013 | Calvosa et al. | 606/249 |
| 2014/0094848 A1* | 4/2014 | Robinson | 606/249 |
| 2014/0114355 A1* | 4/2014 | Robinson | 606/249 |
| 2014/0188170 A1* | 7/2014 | Zappacosta et al. | 606/249 |

FOREIGN PATENT DOCUMENTS

| | | |
|---|---|---|
| DE | 10327230 | 3/2004 |
| DE | 10314072 | 10/2004 |
| EP | 0926994 | 7/1999 |
| EP | 1646341 | 4/2006 |
| FR | 2816197 | 5/2002 |
| FR | 2843693 | 2/2004 |
| WO | 2005/041792 | 5/2005 |
| WO | 2006/084444 | 8/2006 |
| WO | 2010/019783 | 2/2010 |

OTHER PUBLICATIONS

International Preliminary Report on Patentability and Written Opinion, dated Feb. 15, 2011, in related International Application No. PCT/US2009/053727.

International Search Report and Written Opinion, dated Mar. 19, 2010, in related International Application No. PCT/US2009/053727.

* cited by examiner

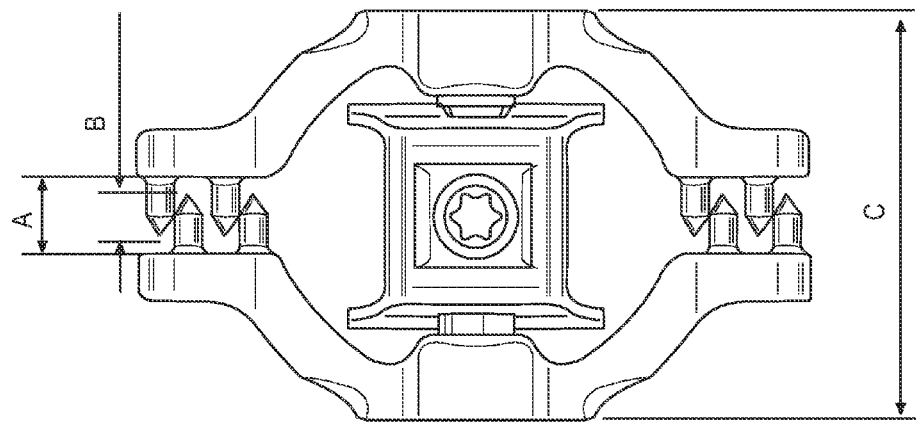
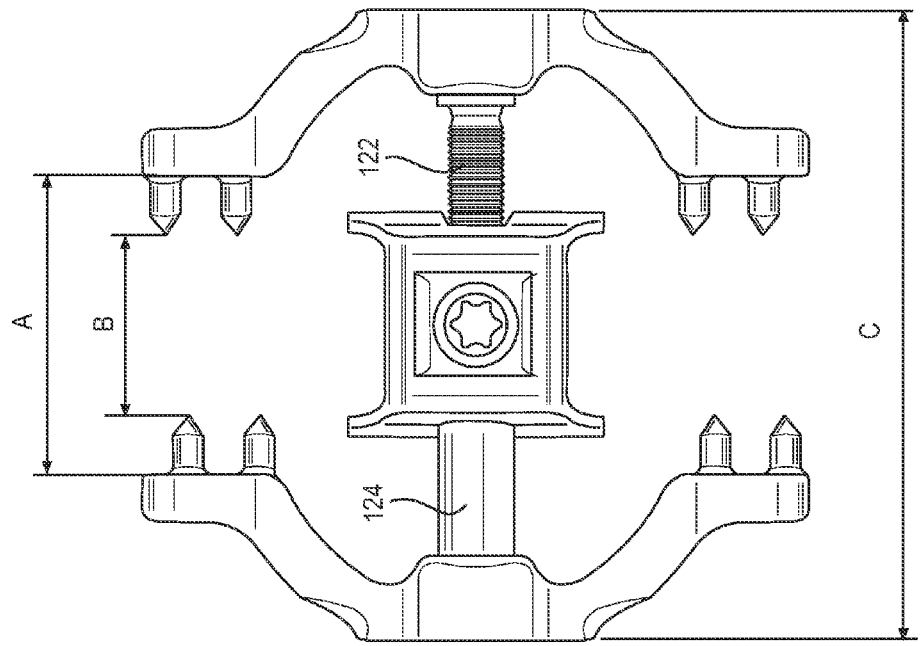

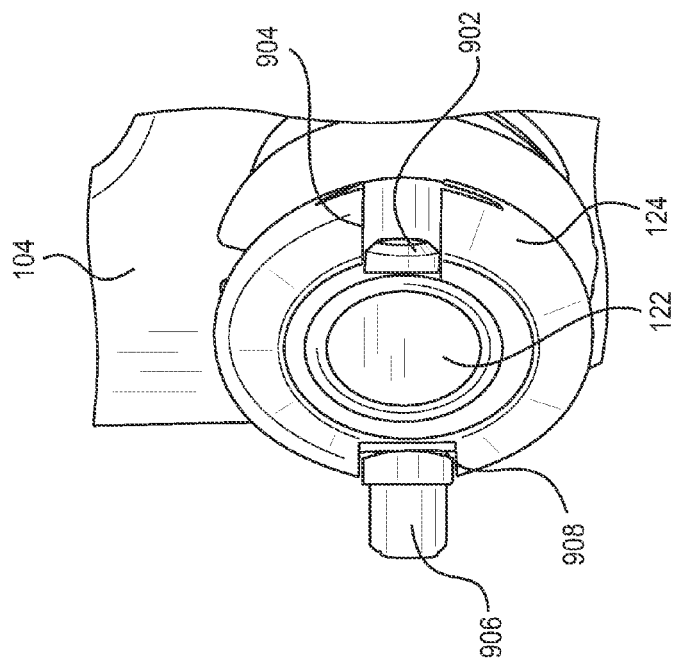
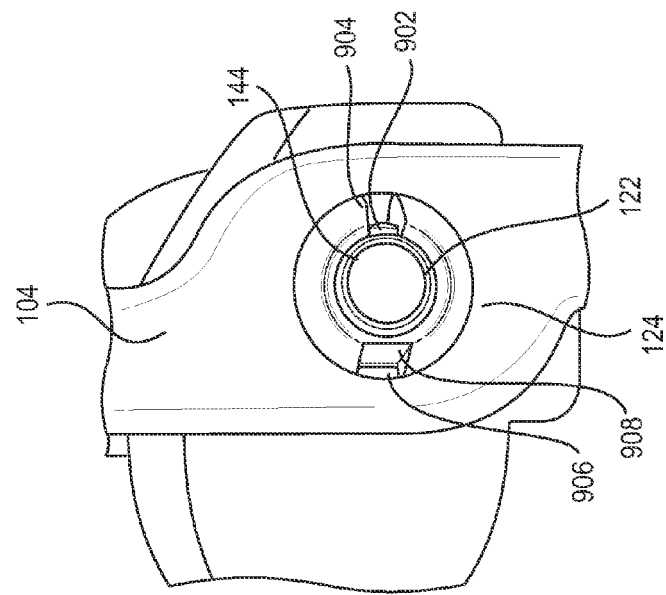

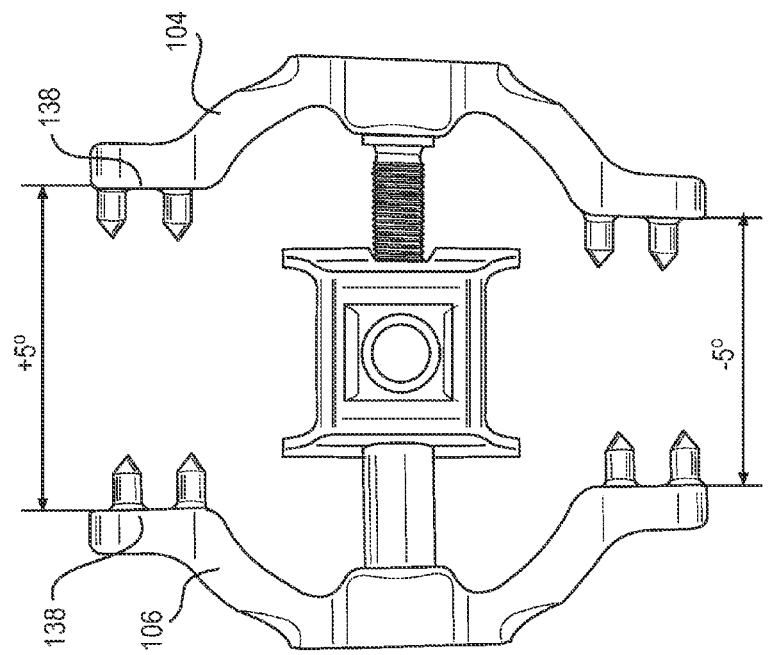
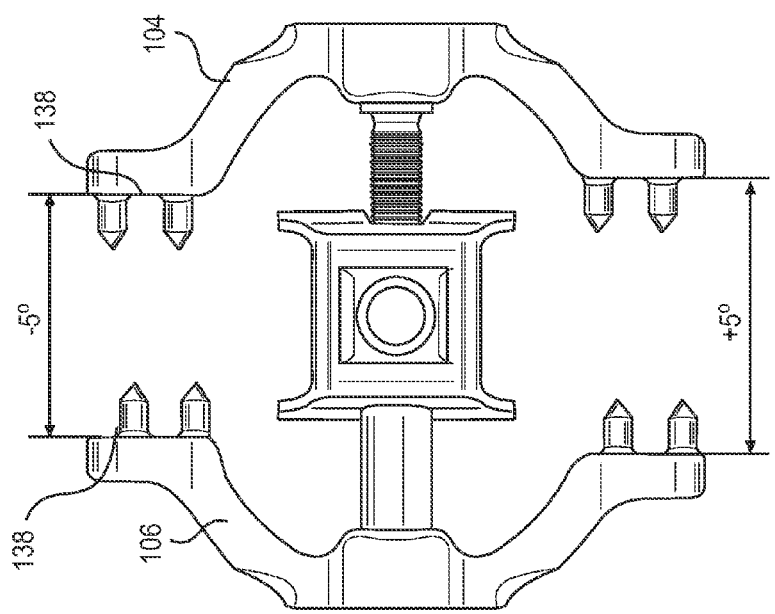

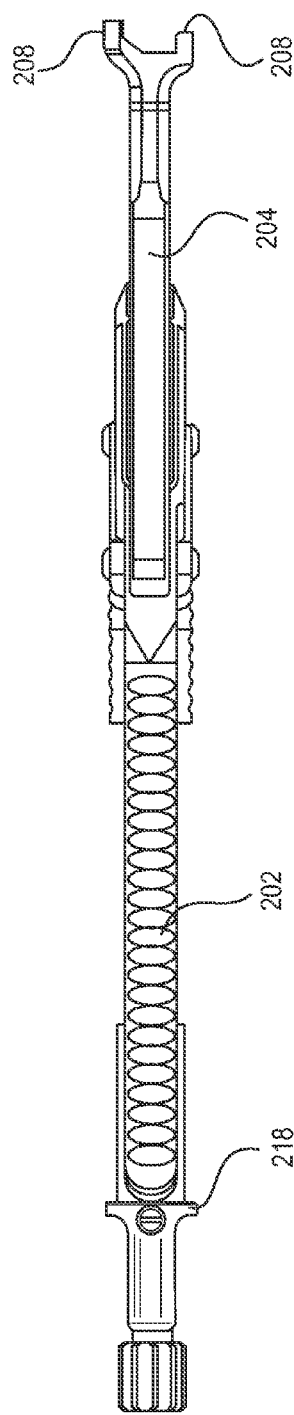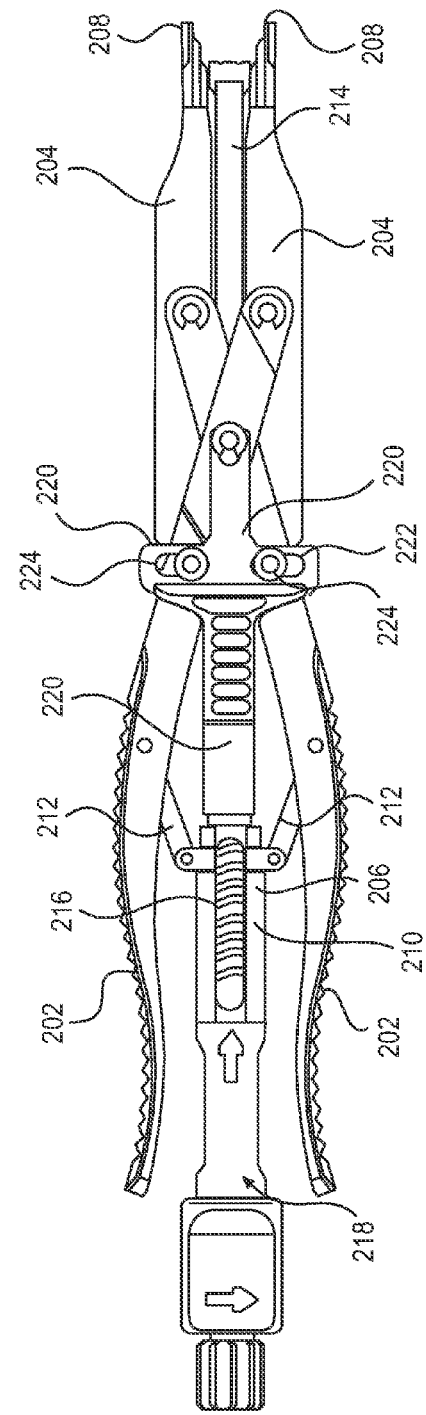

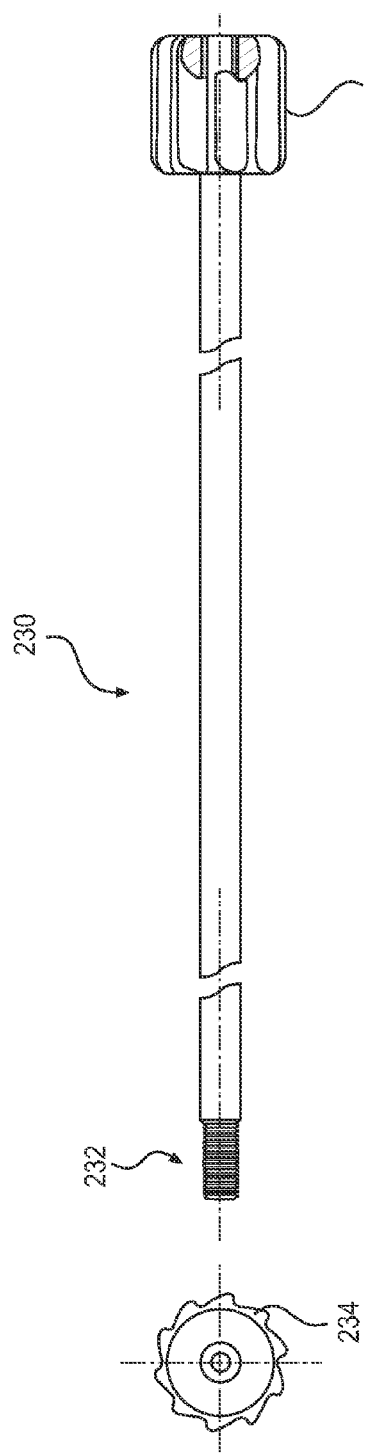
FIG. 14A
FIG. 14B
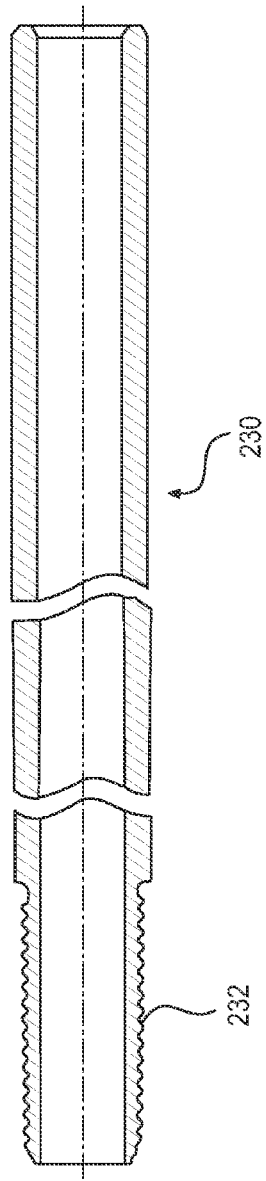
FIG. 14C

SPINOUS PROCESS FIXATOR

TECHNICAL FIELD

This invention relates to generally to orthopedics, and more particularly to an interspinous spacer assembly and associated tools and methods for stabilizing the human spine.

BACKGROUND

A human vertebra has a rearwardly projecting portion known as a spinous process. Bending or the natural aging and degeneration of the spine can cause the adjacent vertebrae and their spinous processes to be moved toward each other. This constricts the space in the spinal canal and foramina and, thus, may cause pain. Such constriction, known as stenosis, can be treated by the use of an implant in the space between adjacent spinous processes.

Generally speaking there are two types of spinal stenosis: (1) hard or rigid spinal stenosis, or (2) soft or dynamic spinal stenosis. In both cases, spinal stenosis may be caused by excessive growth of tissue due to degeneration, loss of disc height, as well as disorders such as spondylolisthesis where the normal relative position and/or orientation of the adjacent vertebrae have been modified.

The most significant difference between the two types of spinal stenosis is generally that dynamic spinal stenosis may be treated with distraction of the vertebra at the affected level while hard stenosis generally requires removal of the tissue that obstructs the spinal canal or foramina at the affected level. In case of tissue removal, the patient generally must accept some loss of stability of the spine. Therefore, it is preferable to increase the stability of the spinal segment by inserting an interspinous spacer between adjacent vertebrae to increase the stiffness of the segment and/or to restrict motion of that segment. Additional stability may be desirable and may be accomplished by adding plates to rigidly fix the spacer to the spinous processes and eliminate motion at that segment (i.e. fusion).

Many spinous process plate systems have a rigid construction that limits their ability to adapt to the varying anatomy of the spinous processes. The large size of many plate systems also limits their use to levels with sufficiently large spinous processes, making them unusable at L5-S1. Additionally, some plate systems consist of multiple pieces which require assembly in-situ. As a result, they sometimes require the simultaneous use of several instruments making the surgical technique and visibility into the operation site difficult. Still other plate systems do not offer an interspinous spacer component to help limit extension of the spine and further stabilize the segment.

Current instrumentation that works with existing spinous process plates requires significant lateral muscle retraction. For instance, in order to lock the plates of the implant to the spinous processes, many instruments compress the implant plates from the outside. This requires additional lateral dissection and muscle retraction to accommodate additional space for the instrument which leads to longer recovery time and healing for the patient. Furthermore, because the forces required to compress the plates can be high, these locking (crimping) instruments can become extremely big and bulky making it difficult for the surgeon to see into the wound. To improve visibility, some systems use smaller instruments but require the simultaneous use of two crimpers instead of one. Some systems require multiple instruments and steps to insert and lock the implant in place.

Thus, there is a need for a spinous process plate system that comes pre-assembled with an interspinous spacer, adapts to the bony anatomy for a wider range of spine levels, and can be easily fixated to the spine. In addition, there is a need for an instrument that can easily insert, crimp, and allow locking of a spinous process plate with minimal lateral muscle retraction while still allowing visualization of the implant.

SUMMARY

The present invention is directed to an interspinous spacer assembly for implantation and/or affixation between spinous processes of adjacent superior and inferior vertebrae and associated tools and methods for stabilizing the human spine. An aspect of the present disclosure is directed to an interspinous spacer assembly for insertion into an interspinous space between spinous processes of adjacent vertebral bodies. The spacer assembly may include a spacer body, a first lateral plate, a second lateral plate and a locking mechanism. The spacer body may be sized and configured for insertion between adjacent spinous processes. The spacer body may include a channel sized and configured to receive the locking mechanism. The first lateral plate and the second lateral plate may couple the spacer assembly to the spinous processes. The locking mechanism may extend through the channel in the spacer body and couple the first and second lateral plates to the spacer body. The locking mechanism may also include a first locking member and a second locking member configured to move relative to each other in a longitudinal direction of the locking mechanism. The second locking member may have a hollow cylindrical body for receiving a body of the first locking member. The body of the first locking member may include an engagement feature sized and configured to releasably engage with a corresponding engagement feature on an interior surface of the hollow cylindrical body of the second locking member.

Another aspect of the present disclosure is directed to a tool for engaging an interspinous spacer assembly for insertion into an interspinous space between spinous processes of adjacent vertebral bodies. The tool may include a handle, a pair of jaws and a linkage mechanism. The pair of jaws may be sized and configured to mate with the interspinous spacer assembly. The linkage mechanism may translate movement of the handle into movement of the pair of jaws. Movement of the pair of jaws, when releasably mated to the interspinous spacer assembly, may cause the interspinous spacer assembly to mate with the spinous processes.

The details of one or more embodiments of the invention are set forth in the accompanying drawings and the description below. Other features, objects, and advantages of the invention will be apparent from the description and drawings, and from the claims.

DESCRIPTION OF DRAWINGS

The device is explained in even greater detail in the following drawings. The drawings are merely examples to illustrate the structure of preferred devices and certain features that may be used singularly or in combination with other features. The invention should not be limited to the examples shown.

FIG. 4A is a back view of an example spacer assembly;

FIG. 4B is a back view of an example spacer assembly;

FIG. 9A is a partial side view of an example first lateral plate and locking mechanism;

FIG. 9B is a partial side view of an example locking mechanism;

FIG. 11A is a back view of an example spacer assembly having articulated lateral plates;

FIG. 11B is a back view of an example spacer assembly having articulated lateral plates;

FIG. 13B is a side plan view of an example crimping tool with the handles closed;

FIG. 13C is a top plan side view of an example crimping tool with the handles closed;

FIG. 14A is an end view of an example cannulated rod;

FIG. 14B is a plan view of an example cannulated rod;

FIG. 14C is a partial cross-section view of an example cannulated rod;

Like reference symbols in the various drawings indicate like elements.

DETAILED DESCRIPTION

Figure 1A:
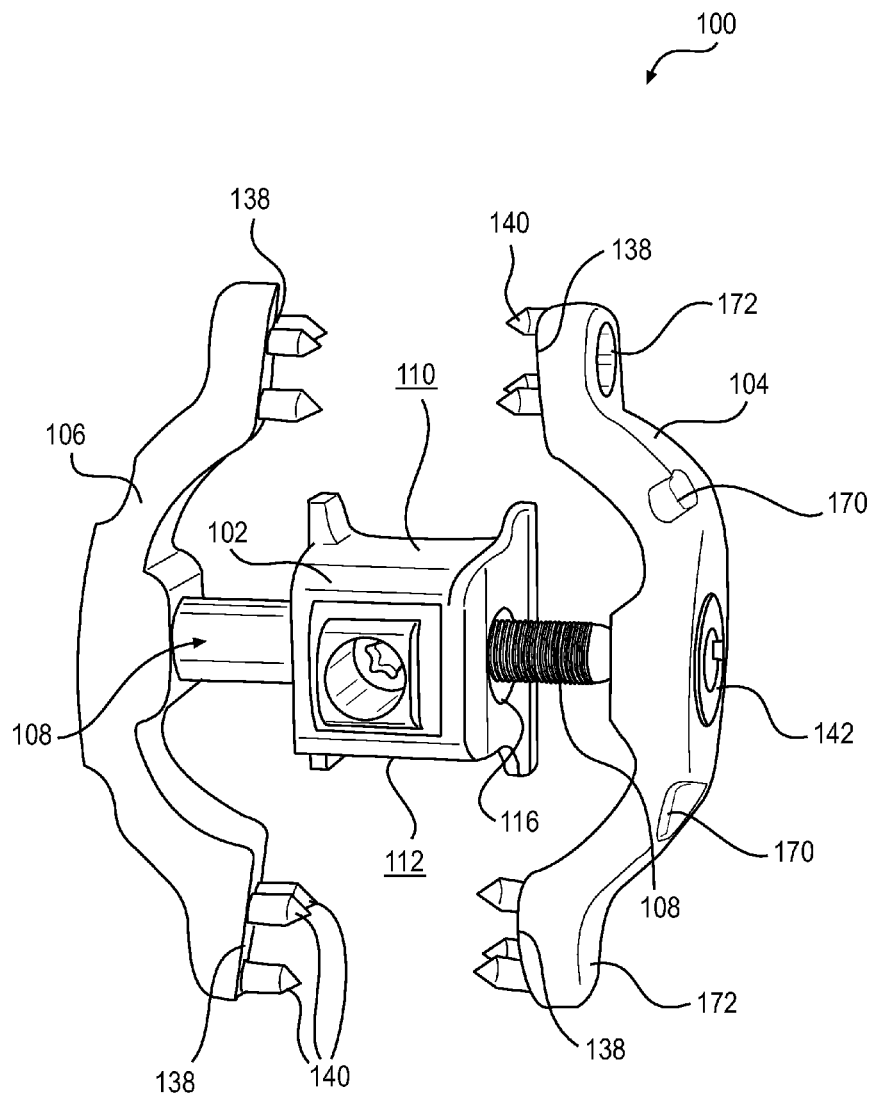
FIG. 1A is a back perspective view of an example spacer assembly.

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

Figure 1B:
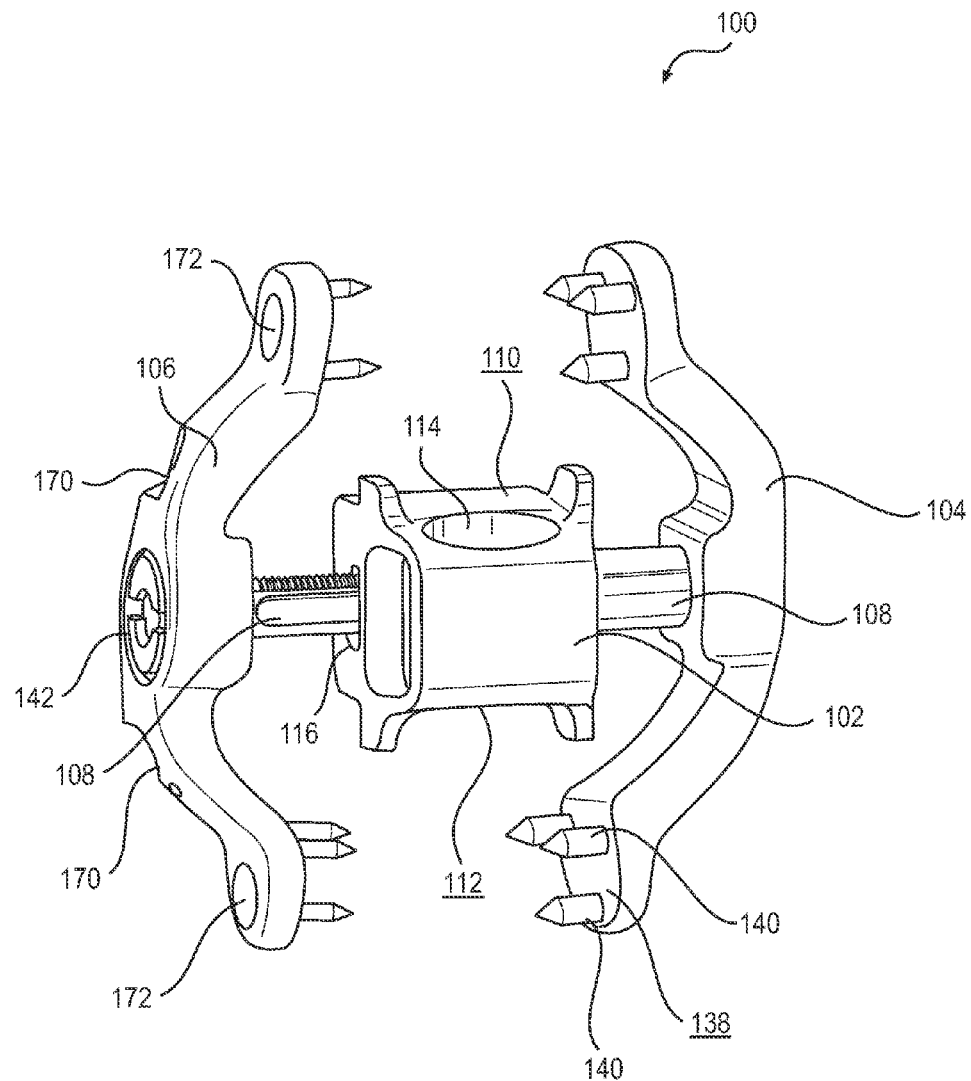
FIG. 1B is a front perspective view of an example spacer assembly.
Figure 1C:
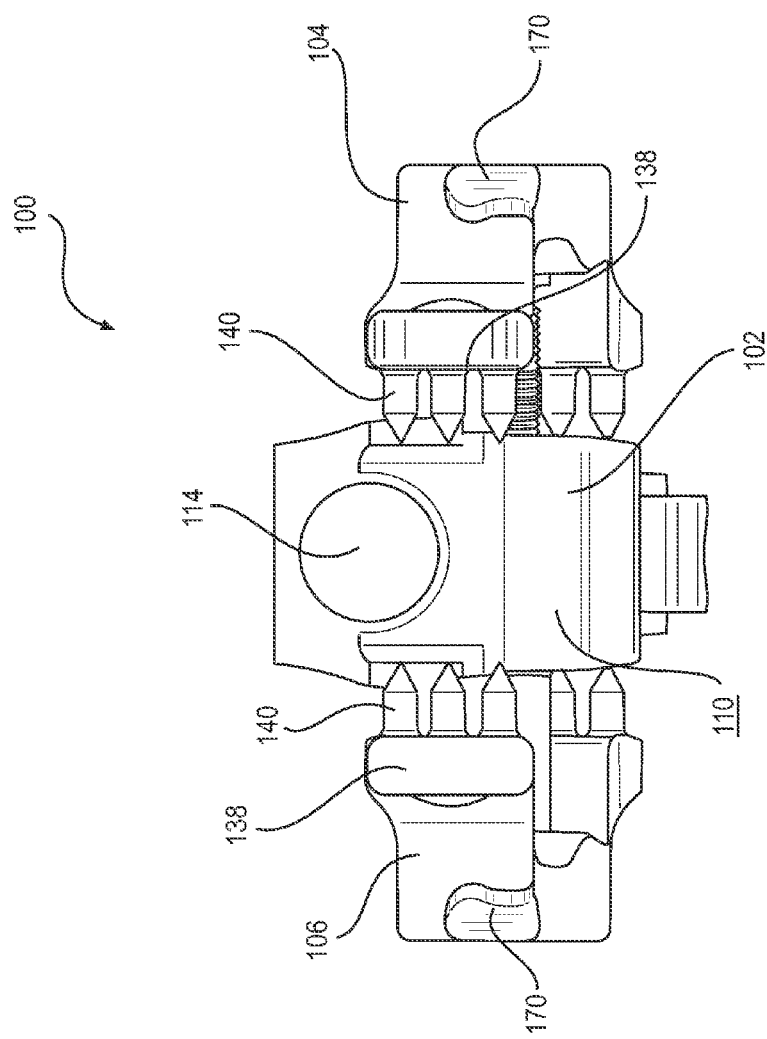
FIG. 1C is a top view of an example spacer assembly.
Figure 2B:
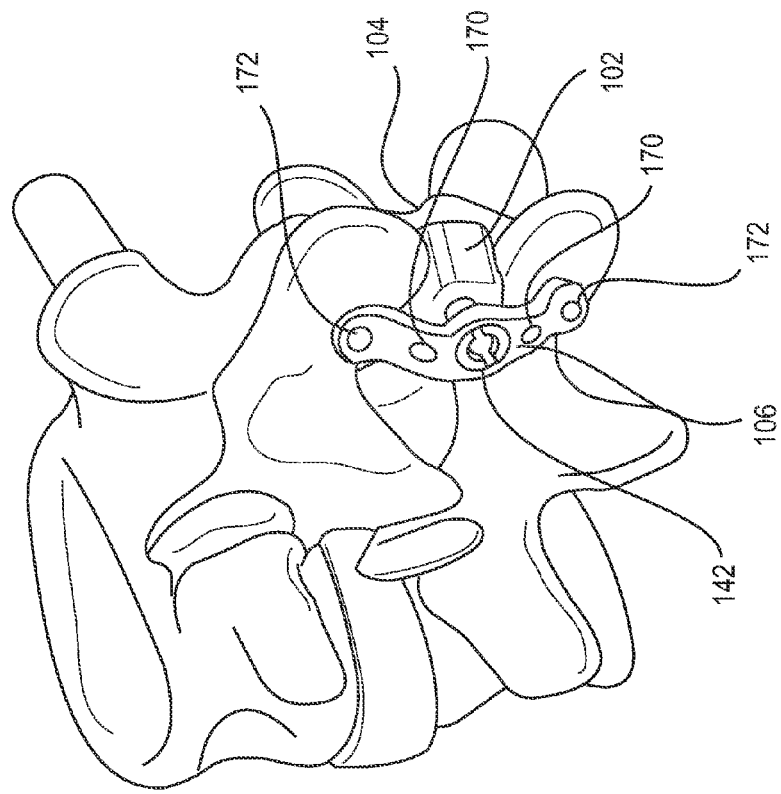
FIG. 2B is a side perspective view of an example spacer assembly between adjacent spinous processes.
Figure 2A:
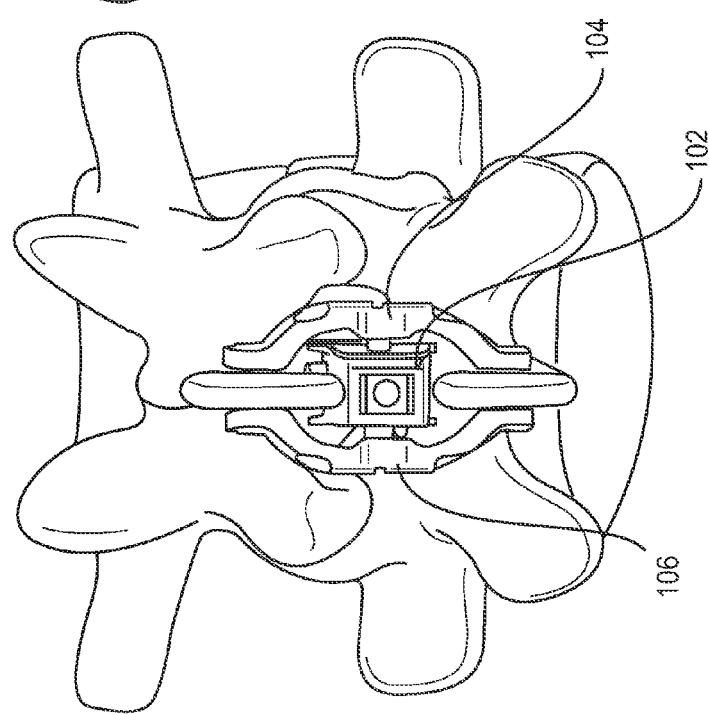
FIG. 2A is a back perspective view of an example spacer assembly between adjacent spinous processes.
Figure 2D:
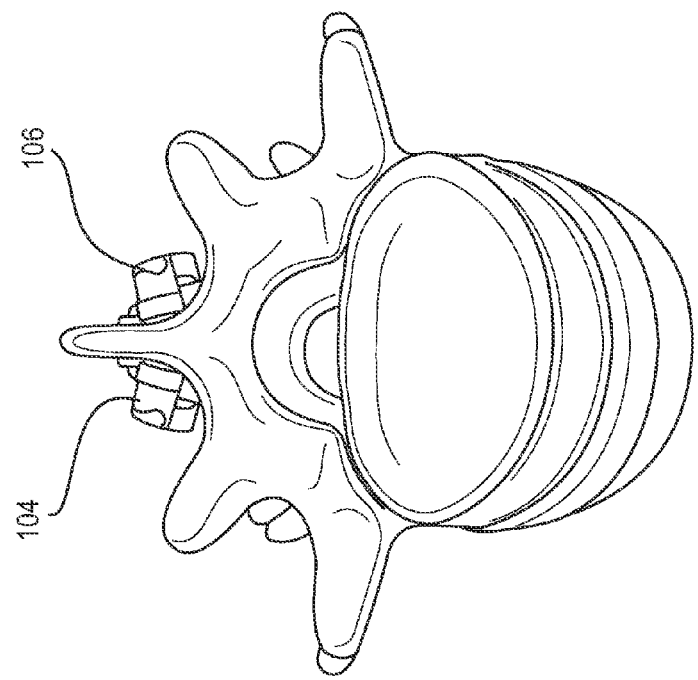
FIG. 2D is a top view of an example spacer assembly between adjacent spinous processes.
Figure 2C:
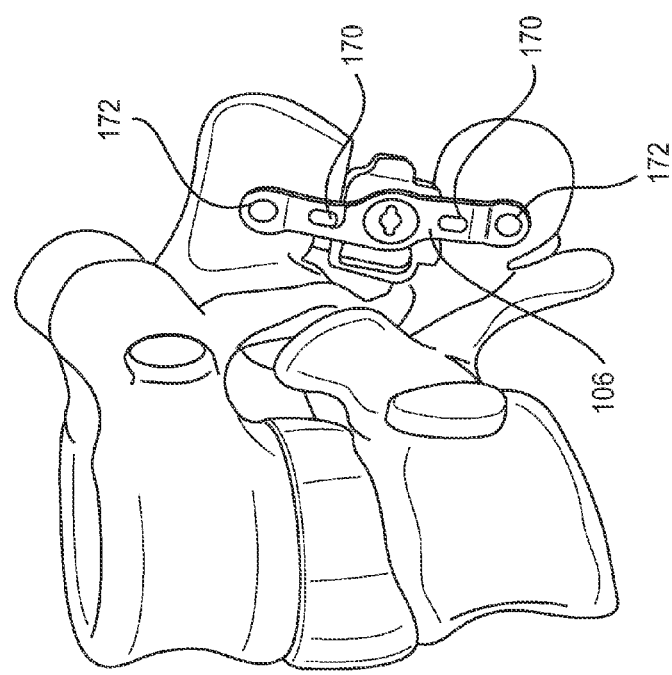
FIG. 2C is a side perspective view of an example spacer assembly between adjacent spinous processes.

In addition, various components may be described herein as extending horizontally along a longitudinal direction "L" and lateral direction "A", and vertically along a transverse direction "T". Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the components merely for the purposes of clarity and illustration and are not meant to be limiting Certain examples of the invention will now be described with reference to the drawings. In general, such embodiments relate to an interspinous spacer assembly 100 for implantation and/or affixation between spinous processes of adjacent superior and inferior vertebrae. FIGS. 1A-1C are front, back and top perspective views of an example interspinous spacer assembly 100. The interspinous spacer assembly 100 can be sized and configured for insertion into an interspinous space between spinous processes of adjacent superior and inferior vertebral bodies. The interspinous spacer assembly 100 includes a spacer body 102, a first lateral plate 104, a second lateral plate 106, and a locking mechanism 108.

The spacer body 102 can be sized and configured for insertion between adjacent spinous processes as illustrated, for example, in FIGS. 2 A-D. An example spacer body 102 can have a generally square/cube shape. The spacer body 102 can include a cranial (top) surface 110 for contacting an inferior (lower) surface of the spinous process of the superior vertebral body. The spacer body 102 can also include a caudal (bottom) surface 112 for contacting a superior (upper) surface of the spinous process of the inferior vertebral body.

The example spacer body 102 can include a cavity 114 sized and configured to receive ostegenic and/or bone graft material. The graft material can help facilitate fusion between the interspinous spacer assembly 100/spacer body 102 and the adjacent spinous processes. The cavity 114 may include one or more bores through the spacer body 102 to accommodate graft material or bone growth therethrough. As illustrated in FIG. 1C, an example cavity 114 can include a throughbore located on an anterior portion of the spacer body 102 running between the cranial (top) surface 110 and the caudal (bottom) surface 112 of the spacer body 102.

The spacer body 102 can include a channel 116 extending through the spacer body 102 between the sides of the spacer body 102. For example, as illustrated in FIGS. 1A, 1B and 5B, the channel 116 can extend through the spacer body 102 between the left and right sides of the spacer body 102. The channel 116 can be sized and configured to receive the locking mechanism 108.

Figure 3B:
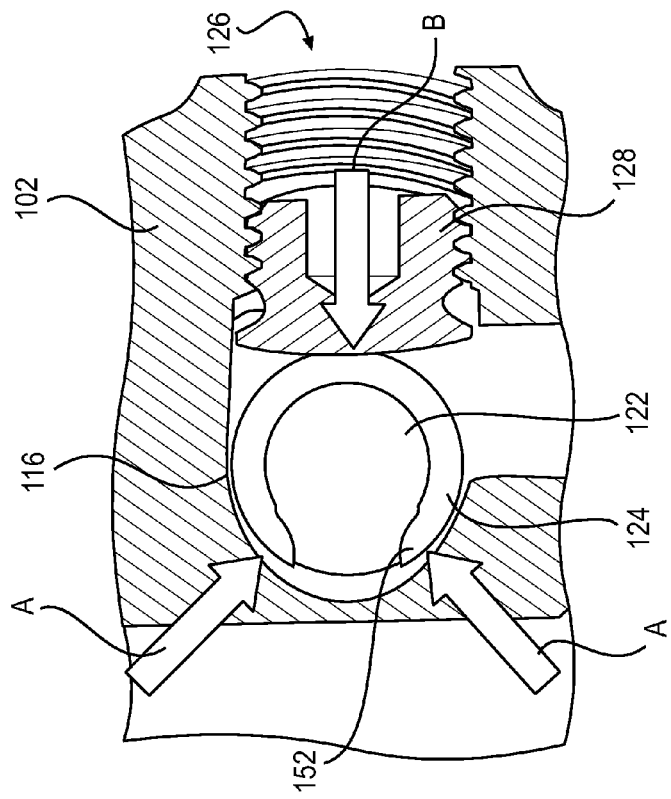
FIG. 3B is a partial cross-section view of a spacer body and locking mechanism.
Figure 3A:
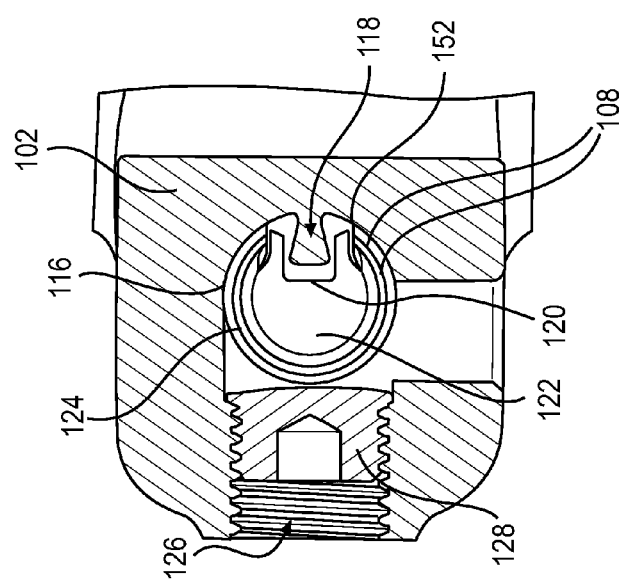
FIG. 3A is a partial cross-sectional view of a spacer body and locking mechanism.

FIG. 3A, provides a cross-section view of the spacer body 102 including the locking mechanism 108. As illustrated in FIG. 3A, the channel 116 can include a channel engagement feature 118. The channel engagement feature 118 can be sized and configured to releasably engage a corresponding engagement feature 120 on the locking mechanism 108. As illustrated in FIG. 3A, the channel engagement feature 118 can include a protrusion extending from the interior surface of the channel 116. The engagement feature 120 of the locking mechanism 108 can include a corresponding recess in the surface of the locking mechanism 108. Interaction between the channel engagement feature 118 and the engagement feature 120 of the locking mechanism 108 can limit lateral and rotational movement of the locking mechanism 108 within the channel 116. For example, lateral movement of the locking mechanism 108 within the channel 116 can be guided by engagement between the channel engagement feature 118 and the engagement feature 120. That is, the locking member 108 can "slide" along the channel engagement feature 118 at the engagement feature 120. Rotational movement of the locking mechanism 108 within the channel 116 can also be controlled by interaction between the channel engagement feature 118 and the engagement feature 120. For example, engagement/interaction between the channel engagement feature 118 and the engagement feature 120 can limit rotation of the locking mechanism 108 within the channel 116. Moreover, the shape and/or clearance between the channel engagement feature 118 and the engagement feature 120 can limit rotation of the locking mechanism 108 within the channel 116 within a predetermined range. For example, as illustrated in FIG. 3A, the clearance and/or shape of the channel engagement feature 118 with respect to the engagement feature 120 can permit limited rotation of the locking mechanism 108 within the channel 116. In a further example, the clearance and/or shape of the channel engagement feature 118 and the engagement feature 120 can prevent all rotational movement of the locking mechanism 108 within the channel 116.

As described in further detail below, the locking mechanism 108 can include a first locking member 122 and a second locking member 124. The channel engagement feature 118 of the locking mechanism 108 can include a recess/channel in the surface of the first locking member 122 and the second locking member 124. In the example spacer assembly 100 illustrated in FIG. 3A, the channel engagement feature 118 includes a recess in the surface of the first locking member 122.

The spacer body 102 can also include a threaded bore 126 sized and configured to receive a set screw 128. The threaded bore 126 can extend from the posterior (back) surface of the spacer body 102 in a direction towards the channel 116, as shown for example in FIGS. 1A, 3A and 3B. In another example (not shown), the threaded bore 126 can extend from the cranial (top) surface 110, the caudal (bottom) surface 112 and/or the anterior (front) surface of the spacer body 102 in a direction towards the channel 116. The set screw 128 can be provided in the threaded bore 126 to engage and fix the position of the locking mechanism 108. For example, once the first and second lateral plates 104, 106 have been positioned against the spinous processes and are sufficiently fixated to the bone, the set screw 128 may be tightened to fix the position of the locking mechanism 108 with respect to the spacer body 102. The set screw 128 can be engaged/tightened against the locking mechanism 108 to fix the position/location of the locking mechanism within the spacer body 102 by pressing the locking mechanism 108 against the wall of the channel 116, as illustrated in FIG. 3B. In the example spacer assembly 100 as illustrated in FIG. 3B, the set screw 128 can be tightened against the first and second locking member 122, 124 (engaged with each other) to press the combined first and second locking member 122, 124 against wall of the channel 116, thereby fixing the location of the locking mechanism 108 with respect to the spacer body 102. The pressure/compressive force provided between the wall of the channel 116 and the set screw 128 on the locking member 108 acts to press the hollow cylindrical body portion 130 of the second locking member 124 against the elongated body 132 of the first locking member 122, as illustrated by arrows A in FIG. 3B. Likewise, the pressure provided by set screw 128 directly on the second locking member 124 can provide an additional (e.g., third) pressure location illustrated by arrow B. The second locking member 124 is thereby compressed against the first locking member 122 and is unable to expand/ratchet over the surface features 134 of the first locking member 122.

Figures 12A, 12B:
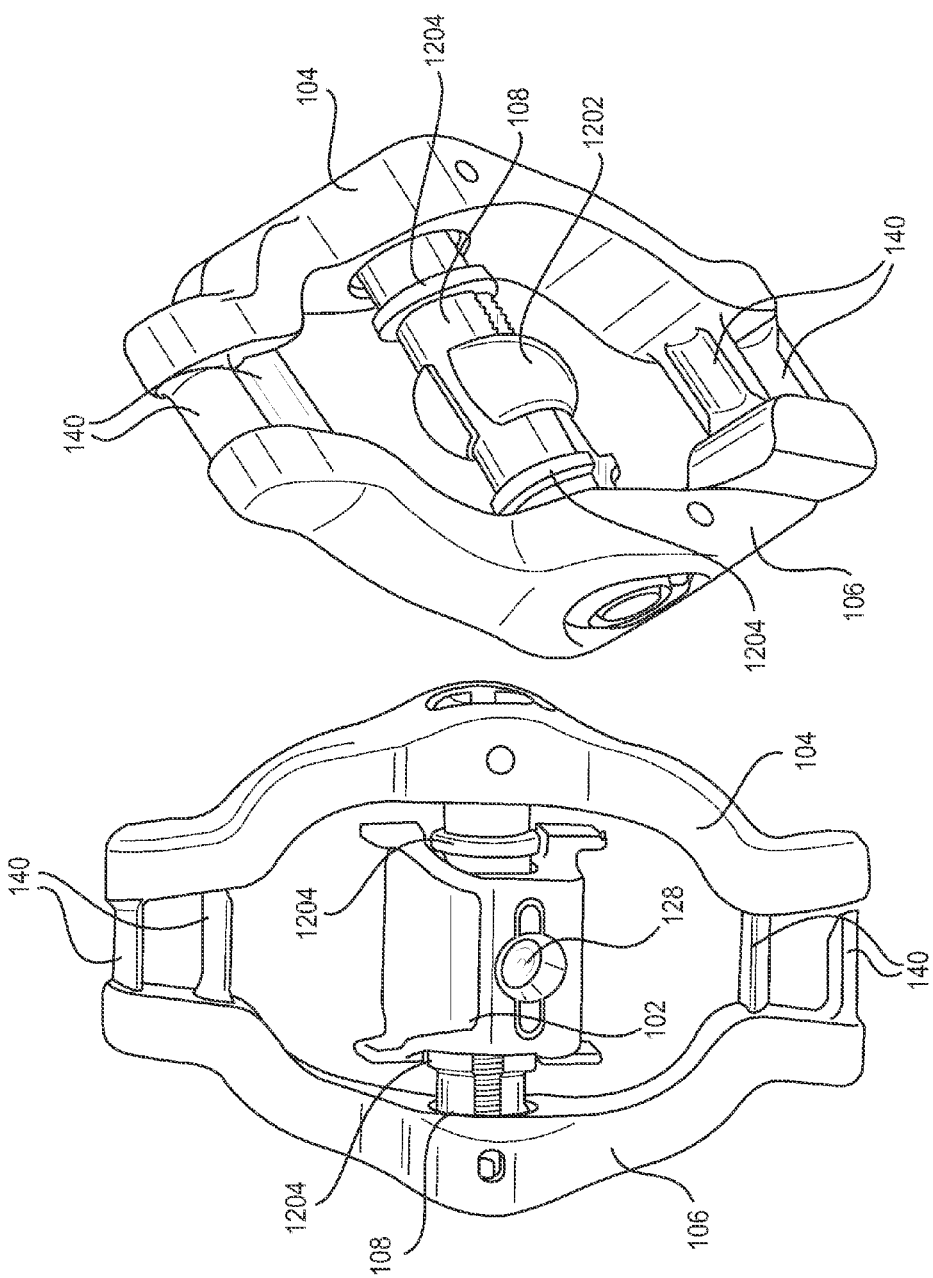
FIG. 12A is a back perspective view of an example spacer assembly.
FIG. 12B is a perspective view of an example spacer assembly with the spacer removed.

Another example spacer assembly 100, illustrated in FIGS. 12A-12C, includes a locking ring 1202 for fixing the location of the locking mechanism 108 with respect to the spacer body 102. FIG. 12B provides a perspective view of a partially exploded spacer assembly 100 excluding the outer surface of the spacer body 102. The spacer assembly 100 can include a locking ring 1202 located along the locking mechanism 108. The locking ring 1202 can include a slot or opening to provide flexibility around the diameter of the locking ring 1202. The set screw 128 can be provided at the threaded bore 126 included in the spacer body 102. When the set screw 128 is tightened, the locking ring 1202 can be deformed against the locking mechanism 108 to fix the position of the locking mechanism 108 with respect to the spacer body 102.

The first lateral plate 104 and the second lateral plate 106 included in the spacer assembly 100 can be sized and configured to couple the spacer assembly 100 to the spinous processes as illustrated in FIGS. 2 A-D. The first and second lateral plates 104, 106 include foot plates 138 for contacting the outer surface of the spinous processes. The surface of the foot plate 138 can be angled to correspond to the anatomy of the spinous process/spine. For example, as illustrated in FIGS. 1A and 1B, the surface of the foot plate 138 can be angled in the frontal plane. That is, the angle of the surface of the foot plate 138 is such that it diverges/intersects with the vertical midplane of the spacer body 102. In another example (not illustrated), the surface of the foot plate 138 can also be angled in the axial (horizontal) plane to correspond to the anatomy of the spinous process/spine.

The foot plate 138 can also include surface features 140 to help secure the spacer assembly 100 to the desired anatomical structures, e.g., spinous process. The surface features 140 can secure the first and second lateral plates 104, 106 to the spinous process via compression. Example surface features 140 can include, for example, projections, spikes, ridges, or teeth, that extend into and/or engage the surface of the spinous process. In an further example (not shown), the surface features 140 can include bolts, rivets, screws, and/or any other form of mechanical connection/fastener known in the art to operatively couple a surgical implant to a vertebral body.

The spacer assembly 100 also includes a locking mechanism 108. The locking mechanism 108 can extend through the channel 116 provided in the spacer body 102 to couple first and second lateral plates 104, 106 to the spacer body 102. The locking mechanism 108 can include a first locking member 122 and a second locking member 124. When viewed from posterior, the first locking member 122 can be located to the right of the spacer body and the second locking member 124 can be located on the left side of the spacer body 102, or vis-a-versa. The first locking member 122 and the second locking member 124 can be co-axial. The proximal ends of the first locking member 122 and the second locking member 124 can be sized and configured couple with the first and second lateral plates 104, 106, respectively. A locking cap 142 can be provided at the proximal ends of the first and second locking members 122, 124 to associate the first and second locking members 122, 124 with the first and second lateral plates 104, 106, respectively. The locking cap 142 can be sized and configured to permit rotational movement of the locking mechanism 108 around its longitudinal axis while fixing the lateral position of the proximal ends of the first and second locking members 122, 124 with respect to the first and second lateral plates 104, 106, respectively. The locking cap 142 can include a surface that corresponds to the size and shape of the heads 144, 146 of the first and second locking members 122, 124. As a result, the locking cap 142 can provide for rotatably engagement the first and second locking member 122, 124 within the first and second lateral plates 104, 106. When the locking cap 142 is fixed to each of the first and second lateral plates 104, 106, the locking mechanism 108 can rotate independently of the locking cap 142 with respect to the first and second lateral plates 104, 106. That is, there is no rotational locking mechanism associated with the locking cap 142 impacting the rotational of the first and second lateral plates 104, 106 with respect to the locking mechanism 108. As a result, stress concentration at the bone fixation interface (foot plates 138) can be reduced and/or minimized.

The first locking member 122 and the second locking member 124 can be configured to move relative to each other in the longitudinal direction of the locking mechanism 108. For example, the first and second locking members 122, 124 when engaged can create a telescoping effect with respect to the proximal ends of each of the first and second locking members 122, 124. As illustrated in FIGS. 4A and 4B, the first and second locking members 122, 124 can be adjusted so as to control the lateral distance between the first and second lateral plates 104, 106 coupled to the proximal ends of each of the first and second locking members 122, 124, respectively.

FIG. 4A provides an example spacer assembly 100 with the first and second locking members 122, 124 in a spaced apart or open configuration. In the spaced apart or open configuration, the first and second lateral plates 104, 160 can fit around the spinous process during installation of the spacer assembly 100. In an example spacer assembly 100 in an open configuration, the distance between opposing foot plates 138, measurement A, can be about 0 mm to about 16 mm. In another example, the minimum distance between opposing foot plates 138 in a fully open configuration is at least about 16 mm. In a further example, the maximum distance between opposing foot plates 138 in a fully open configuration is about 16 mm.

Likewise, in an open configuration the distance between opposing surface features 140 (e.g., teeth), measurement B can be determined to provide sufficient clearance between the surface features 140 and the spinous process during installation. For example, the measurement B can be about 0 mm and about 10 mm. In another example, the minimum distance between opposing surface features 140 in a fully open configuration is at least about 9.4 mm. In a further example, the maximum distance between opposing surface features 140 in a fully open configuration is about 9.4 mm.

In an open configuration, the width of the first and second lateral plates 104, 106, measurement C can be determined to minimize the amount of lateral retraction. For example, the width, measurement C in an open configuration can be about 17 mm to about 34 mm. In another example, the minimum width of the first and second lateral plates 104, 106 in a fully open configuration is at least about 33.6 mm. In a further example, the maximum width of the first and second lateral plates 104, 106 in a fully open configuration is about 33.6 mm.

FIG. 4B illustrates an example spacer assembly 100 with the first and second locking members 122, 124 in a together or closed configuration. In the closed configuration, the first and second lateral plates 104, 106 can contact or engage the spinous process for installation of the spacer assembly 100. Though not illustrated in FIG. 4B, amount of contact/engagement of the surface features 140 with the adjacent spinous processes during installation can be determined based on patient anatomy. As illustrated in FIG. 4B, the foot plates 138 can include surface features 140 that are sized and configured such that the surface features 140 to not interfere with each other when the assembly 100 is in the closed configuration. In another example (not shown), the surface features 140 may be sized and configured to interfere, engage, or otherwise impact each other when the spacer assembly 100 is in the closed configuration.

In an example spacer assembly 100 in a closed configuration, the distance between opposing foot plates 138, measurement A, can be about 0 mm to about 6 mm. In another example, the minimum distance between opposing foot plates 138 in a closed configuration is at least about 4.1 mm. In a further example, the maximum distance between opposing foot plates 138 in a closed configuration is about 4.1 mm.

Likewise, in a closed configuration the distance between opposing surface features 140 (e.g., teeth), measurement B, can be about 0 mm and about −4 mm (4 mm overlap). In another example, the minimum distance between opposing surface features 140 in a closed configuration is at least about −2.5 mm (2.5 mm overlap). In a further example, the maximum distance between opposing surface features 140 in a closed configurations is about −2.5 mm (2.5 mm overlap).

In a closed configuration, the width of the first and second lateral plates 104, 106, measurement C, can be about 17 mm to about 25 mm. In another example, the minimum width of the first and second lateral plates 104, 106 in a closed configuration is at least about 21.7 mm. In a further example, the maximum width of the first and second lateral plates 104, 106 in a closed configuration is about 21.7 mm.

As described above, the first locking member 122 and the second locking member 124 can be configured to move relative to each other in the longitudinal direction of the locking mechanism 108. As illustrated in FIGS. 5A-5D, in an example spacer assembly 100, the first locking member 122 includes a head 144, an elongated body 132, and a neck portion 148 located between the head 144 and the elongated body 132. Likewise, the second locking member 124 includes a head 146, a hollow cylindrical body portion 130, and a neck portion 150 located between the hollow cylindrical body portion 130 and the head 146.

Figure 5A:
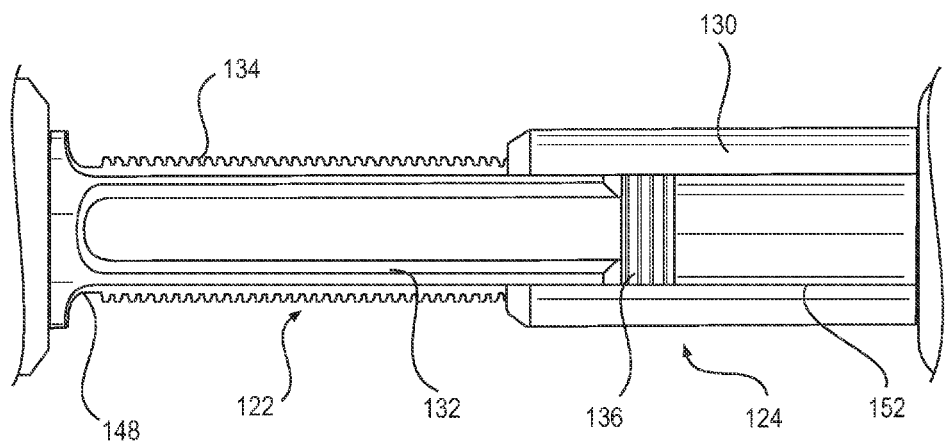
FIG. 5A is a partial front view of an example locking mechanism.
Figure 5B:
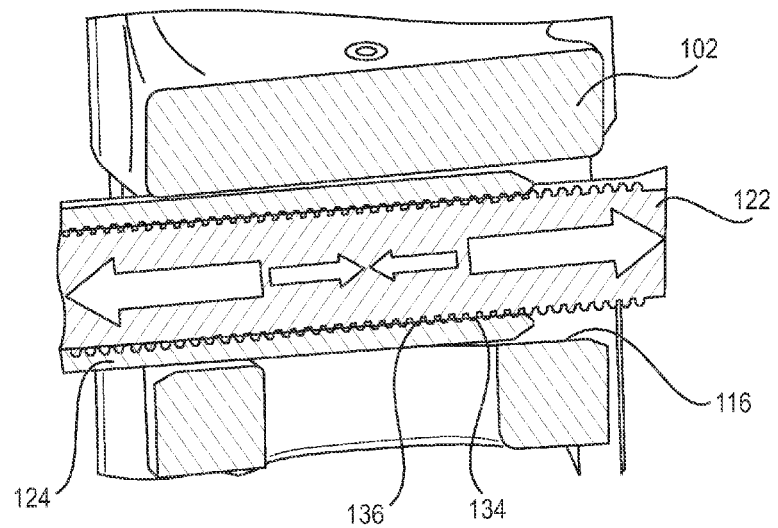
FIG. 5B is a partial cross-section view of the a spacer body and locking mechanism.

As illustrated in FIGS. 5A and 5B, the elongated body 132 of the first locking member 122 can be sized and configured to fit within the elongated hollow cylindrical body portion 130 of the second locking member 124. In an example spacer assembly 100, the first and second locking members 122, 124 can comprise a set of interlocking male and female bolts. The first locking member 122 can include a surface feature 134 extending from an outer surface of the elongated body portion 132. For example, the surface feature 134 can include a projection, thread, spike, ridge, or tooth extending from the outer surface of the first locking member 122. The surface feature 134 can also include a series of projections, spikes, ridges, or teeth extending from the outer surface of the first locking member 122. The surface feature 134 can be located along the entire length of the elongated body portion 132. In another example, the surface feature 134 is located along only a portion of the elongated body portion 132.

Figure 5C:
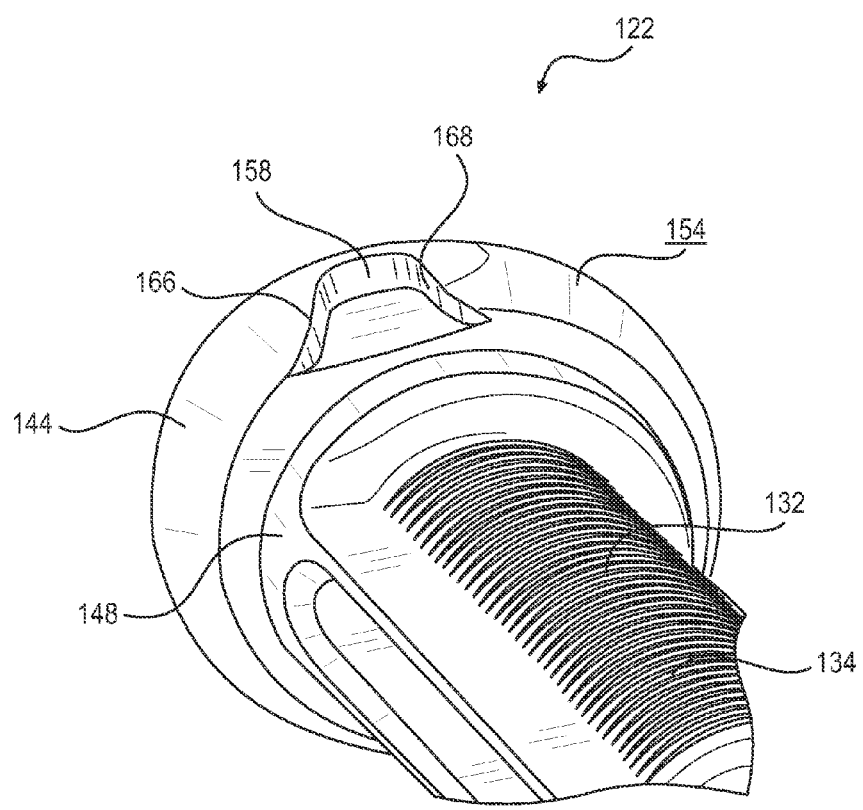
FIG. 5C is a partial perspective view of an example first locking member.
Figure 5D:
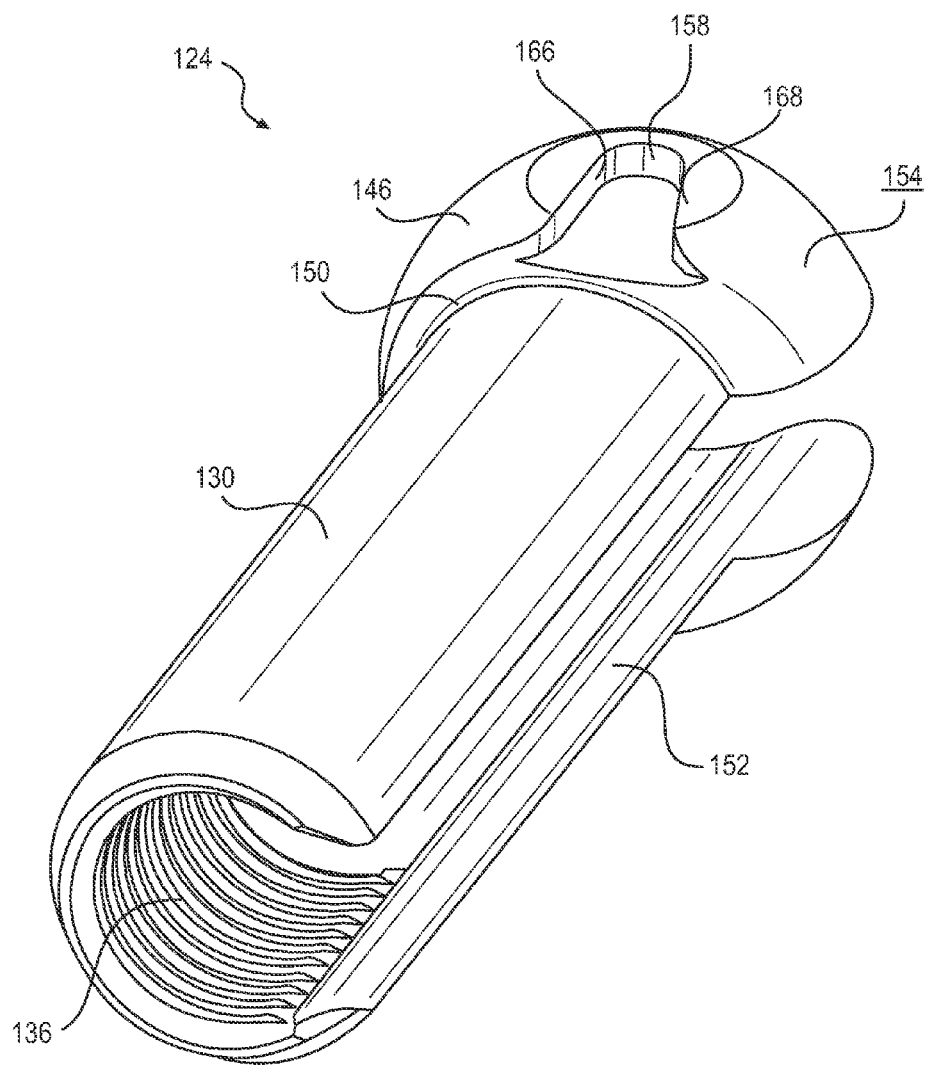
FIG. 5D is a partial perspective view of an example second locking member.

The second locking member 124 can include a surface feature corresponding to surface feature 134. The second surface feature 136 can be sized and configured to correspond to the surface feature 134 of the first locking member 122. The second surface feature 136 may be sized and configured to matingly engage the surface feature 134 of the first locking member 122. The second surface feature 136 can include a hollow or recess located on an interior surface of the hollow cylindrical body portion 130. Likewise, the second surface feature 136 can include a series of hollows or recesses located on the interior surface of the hollow cylindrical body portion 130. As illustrated in FIGS. 5A, 5B and 5D, the second surface feature 136 can be located along a portion of the interior surface of the hollow cylindrical body portion 130. In another example (not shown), the second surface feature 136 can be located along the entire length of the interior surface of the hollow cylindrical body portion 130.

The interaction between the surface feature 134 and the second surface feature 136 can be used to control the longitudinal spacing of the first and second locking members 122, 124 and first and second lateral plates 104, 106, respectively. Engagement of sequential surface features 134 and second surface features 136 can create a ratchet-like effect when adjusting the longitudinal spacing of the first and second locking members 122, 124. In an example spacer assembly 100, the surface feature 134 is asymmetrical with respect to the second surface feature 136. For example the size, shape and/or location of the surface features 134 may not directly correlate to the size, shape and/or location of the corresponding second surface features 136. The asymmetry of the surface features 134 and the second surface features 136 can be configured such that laterally movement of the proximal ends of each of the locking members towards each other (i.e., movement of the first and second lateral plates 104, 106 towards each other/movement in the direction of a closed configuration) can require less force than movement in the opposite direction (i.e., movement of the first and second lateral plates 104, 106 away from each other/movement in the direction of an open configuration). In an example spacer assembly 100, the first and second locking members 122, 124 are moved toward a closed configuration via compressive force at the proximal ends of the first and second locking members 122, 124. The asymmetry of the surface features 134 and the second surface features 136 can be configured such that the compressive force required to move the first and second locking members 122, 124 towards each other is less than the tensile force required to move the first and second locking members 122, 124 in the opposite (open) direction.

As described above, with respect to FIG. 3A, the locking member 108 can include an engagement feature 120 can include a recess in the surface of the first locking member 122. The second locking member 124 can include an opening 152 to provide access between the engagement feature 120 (first locking member 122) and the channel engagement feature 118 (spacer body 102). As illustrated in FIG. 5D, the opening 152 can be provided along the length of the hollow cylindrical body portion 130. In another example, the opening 152 can be provided along a portion of the length of the hollow cylindrical body portion 130. As illustrated in FIGS. 3A, 3B and 5D, the second locking member 124, including the opening 152, can define a C-shaped cross-section. The opening 152 can also provide flexibility to the hollow cylindrical body portion 130. For example, the opening 152 can enable the hollow cylindrical body portion 130 to expand and contract as the surface features 134 of the first locking member 122 engage and disengage the second surface features 136 of the second locking member 124.

The first locking member 122 and the second locking member 124 include heads 144, 146. As illustrated in FIGS. 5C, 5D, 7 A-C and 8 A-B, the heads 144, 146 can include a curved surface 154 sized and configured to correspond to a curved cavity/surface 156 included in each of the first and second lateral plates 104, 106. The curved surface 154 permits the first and second locking members 122, 124 to rotate and articulate/pivot freely (in any direction) with respect to the first and second lateral plates 104, 106. Rotation and articulation of the first and second lateral plates 104, 106 permits the spacer assembly 100 to better accommodate the varying anatomy of the spinous process. The rotation and articulation of the first and second lateral plates 104, 106 also permits multiple spacer assemblies 100 to be placed on adjacent spinous processes. That is, multiple foot plates 138 can be located on the same spinous process in an offset configuration.

The curved cavity/surface 156 can also prevent lateral movement of the first and second locking member 122, 124 with respect to the first and second lateral plates 104, 106 in the inward direction, in the direction towards a closed configuration. That is, the curved cavity/surface 156 can define the lateral/longitudinal location of the proximal end with respect to the first and second locking member 122, 124.

Figure 6B:
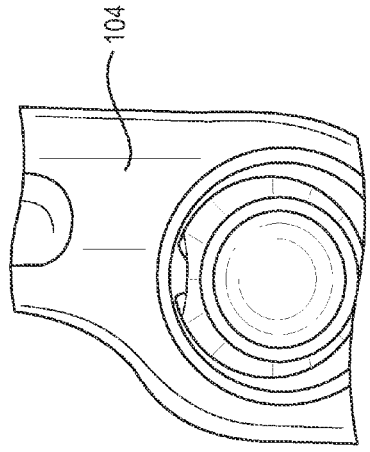
FIG. 6B is a partial side view of an example first lateral plate and first locking member.
Figure 6A:
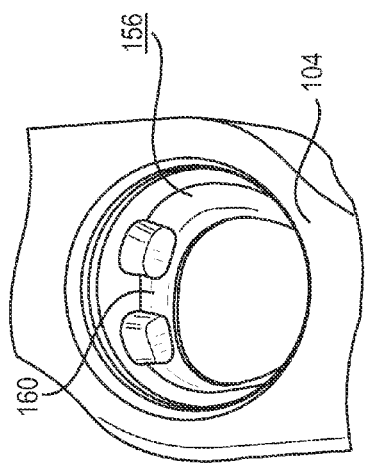
FIG. 6A is a partial perspective view of an example first lateral plate.

With respect to rotational movement, the interface between the heads 144, 146 and the first and second lateral plates 104, 106 can be configured to limit rotational movement between the locking mechanism 108 (locking members 122, 124) and the lateral plates 104, 106. For example, as illustrated in FIG. 5C, the head 144 of the first locking member 122 (and/or the second locking member 124 illustrated in FIG. 5D) can include a head engagement feature 158 sized and configured to matingly engage a corresponding plate engagement feature 160 on the first lateral plate 104 (FIG. 6A). In an example spacer assembly 100, the head engagement feature 158 includes a recess sized and configured to mate with a corresponding protrusion or key provided in the first lateral plate 104, i.e., plate engagement feature 160.

Figure 6C:
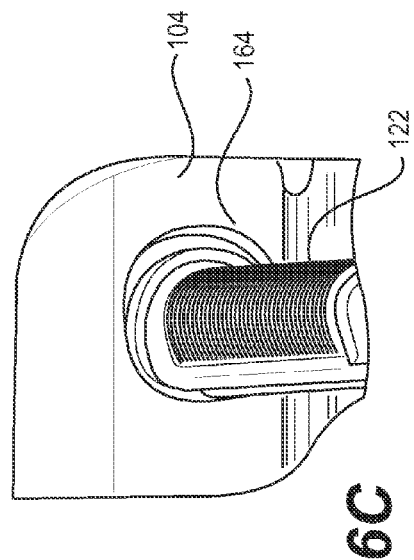
FIG. 6C is a partial side view of an example first lateral plate and first locking member.
Figure 7A:
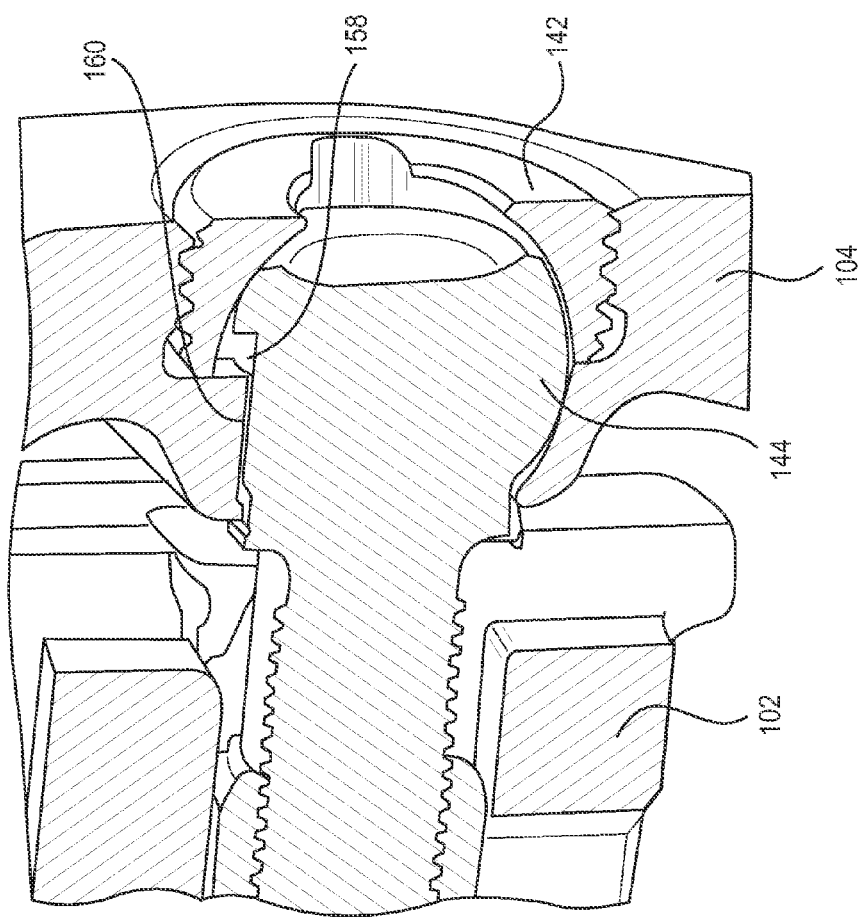
FIG. 7A is a partial side cross-section view of the a spacer body and locking mechanism.
Figure 7B:
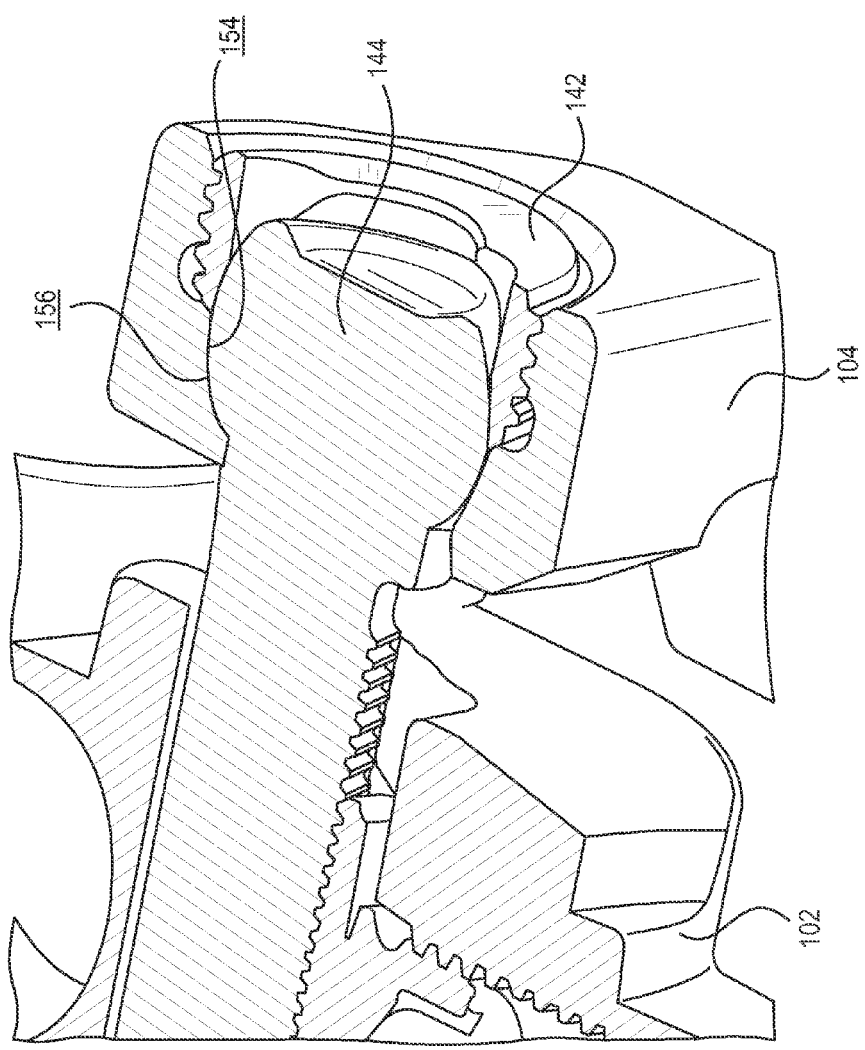
FIG. 7B is a partial top cross-section view of the a spacer body and locking mechanism.

FIG. 6A illustrates the curved cavity 156 and the plate engagement feature 160 included in the first lateral plate 104 for receiving and engaging the first locking member 122. FIGS. 6B and 6C illustrate right and left views of the first locking member 122 located within the first lateral plate 104 with the locking cap 142. FIG. 7A provides a side cross-section view of the spacer body 102 and locking mechanism 108 and FIG. 7B provides a top cross-section view of the spacer body 102 and the locking mechanism 108 where the head engagement feature 158 is engaged with the plate engagement feature 160. As shown in FIGS. 6A and 7A, the plate engagement feature 160 can be provided on in the curved cavity/surface 156 and the head engagement feature 158 can be provided on the curved surface 154. In another example (not shown), the plate engagement feature 160 can be included on the bore 162 provided in the first lateral plate 106. Likewise, the head engagement feature 158 can be provided on a surface of the first locking member 122 other than the curved surface 154 including, for example, on the neck 148, the head 144 and/or the elongated body portion 132.

The interaction between the head engagement feature 158 and the plate engagement feature 160 can limit the rotational movement between the first locking member 122 and the first lateral plate 104. For example, the interaction between the head engagement feature 158 and the plate engagement feature 160 can limit rotation of the first lateral plate 104 about the longitudinal axis of the locking mechanism 108. For example, the plate engagement feature 160 and the head engagement feature 158 can be configured to prevent all rotational movement of the first locking member 122 with respect to the first lateral plate 104. In another example, the plate engagement feature 160 and the head engagement feature 158 can be configured to such that rotational movement can be limited within a predetermined range. The clearance and/or shape of the head engagement feature 158 with respect to the plate engagement feature 160 can determine the range of rotation. As illustrated in FIG. 5C, the head engagement feature 158 can include a first wall 166 and a second wall 168 defining the width of the recess. The clearance between the head engagement feature 158 and the plate engagement feature 160 (e.g., difference between the width of the recess defined by the first wall 166 and the second wall 168 and the width of the plate engagement feature 160) can determine the range of rotational movement. As illustrated in FIG. 5C, the first wall 166 and the second wall 168 can be provided at an angle divergent with the longitudinal axis of the first locking member 122 to provide for additional rotational movement between the first locking member 122 and the first lateral plate 104 within a predetermined range.

Figure 8A:
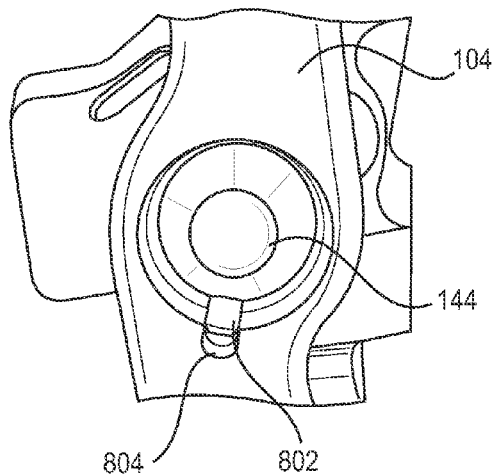
FIG. 8A is a partial side view of an example first lateral plate and first locking member with the locking cap removed.
Figure 8B:
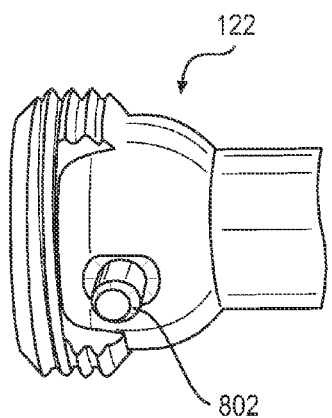
FIG. 8B is a partial view of an example first locking member with the locking cap removed.
Figure 8C:
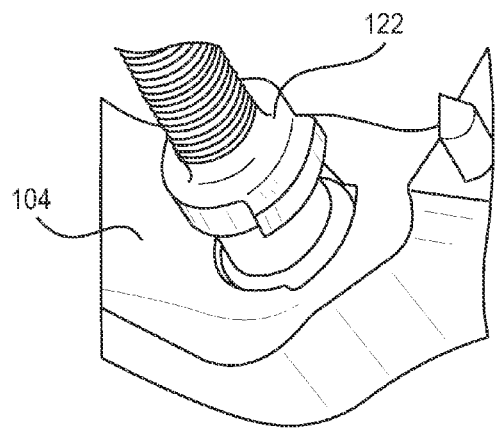
FIG. 8C is a partial side view of an example first lateral plate and first locking member.

In a further example of the spacer assembly 100 illustrated in FIGS. 8A-8C, the head 144 of the first (and/or second) locking member 122 can include a pin-like protrusion 802 extending from the surface of the head 144 for limiting rotation of the first locking member 122 with respect to the first lateral plate 104. The protrusion 802 can be sized and configured to mate with a corresponding slot 804 in the first (and/or second) lateral plate 104. Interference of the protrusion 802 and the slot 804 can prevent rotation of the first locking member 122 with respect to the first lateral plate 104.

In another example of the spacer assembly 100 illustrated in FIGS. 9A and 9B, the head 144 of the first (and/or second) locking member 122 can include a first pin 902 that is received within a bore included in the first locking member 122 and engages/mates with a corresponding bore or slot 904 in the second locking member 124, thereby limiting rotation of the first locking member 122 with respect to the second locking member 124. The spacer assembly 100 can also include a second pin 906 received within a bore included in the first (and/or second) lateral plate 104 that engages a corresponding bore or slot 908 in the outer surface of the second locking member 124. The second pin 906 can prevent disassembly of the first locking member 122 from the first (and/or second) lateral plate 104. The second pin 906 can also limit rotation of the first locking member 122 with respect to the first (or second) lateral plate 104.

Figure 10B:
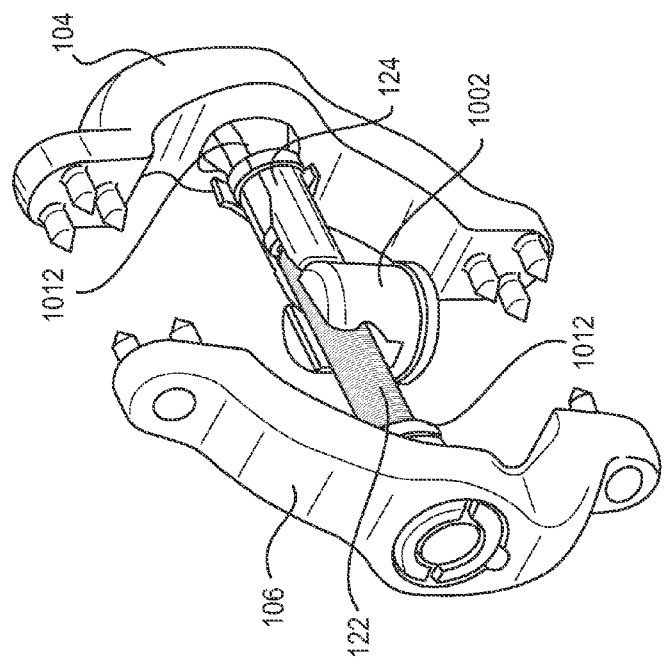
FIG. 10B is a front perspective view of an example spacer assembly with the spacer removed.
Figure 10A:
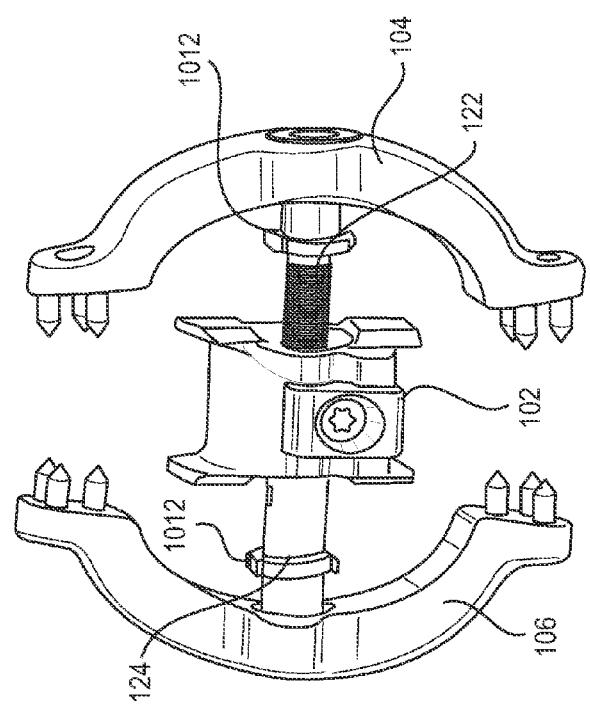
FIG. 10A is a back perspective view of an example spacer assembly.
Figure 10C:
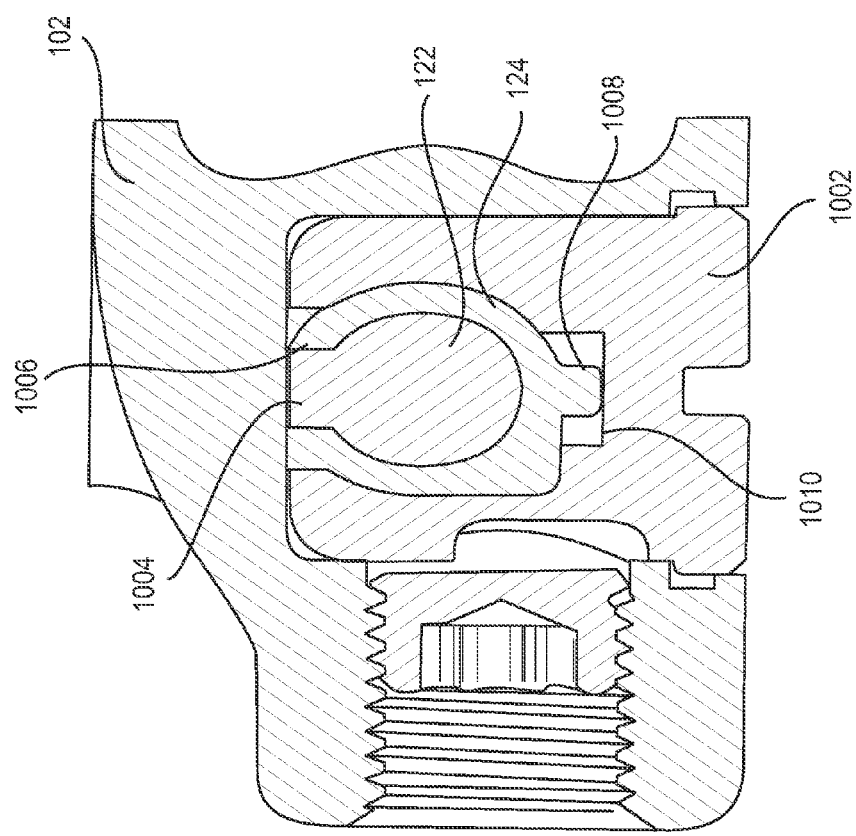
FIG. 10C is a partial side cross-section view of the a spacer body including a cylindrical bearing.

In further example spacer assembly 100, illustrated in FIGS. 10A-10C, includes a cylindrical bearing 1002 used to allow limited rotation around the bearing 1002 axis in addition to limiting rotation around the longitudinal axis of the locking mechanism 108. FIG. 10B provides a perspective view of a partially exploded spacer assembly 100 excluding the outer surface of the spacer body 102. The cylindrical bearing 1002 can be provided inside the spacer body 102 to allow rotation around the longitudinal axis of the locking mechanism 108. As illustrated in FIG. 10C, a side cross-section view of the spacer body 102 including the cylindrical bearing 1002 and the first and second locking members 122, 124, the first locking member 122 can include a first engagement feature 1004 sized and configured to engage a second engagement feature 1006 included on the second locking member 124. For example, the first engagement feature 1004 can include a protrusion or key extending from the surface of the first locking member 122 and the second engagement feature 1006 can include a slot or opening in the second locking member 124. The protrusion (first engagement feature 1004) can engage the slot (second engagement feature 1006) and limit the rotation of the first locking member 122 with respect to the second locking member 124 along the longitudinal axis of the locking mechanism 108. The second locking member 124 can include a third engagement feature 1008 sized and configured to engage a forth engagement feature 1010 included on the cylindrical bearing 1002. The third engagement feature 1008 can include a protrusion or key extending from the outer surface of the second locking member 124 and the forth engagement feature 1010 can include a corresponding groove/slot in the cylindrical bearing 1002. The protrusion (third engagement feature 1008) can engage the slot (forth engagement feature 1010) and limit the rotation of the second locking member 124 with respect to the spacer body 102/cylindrical bearing 1002.

Figure 11D:
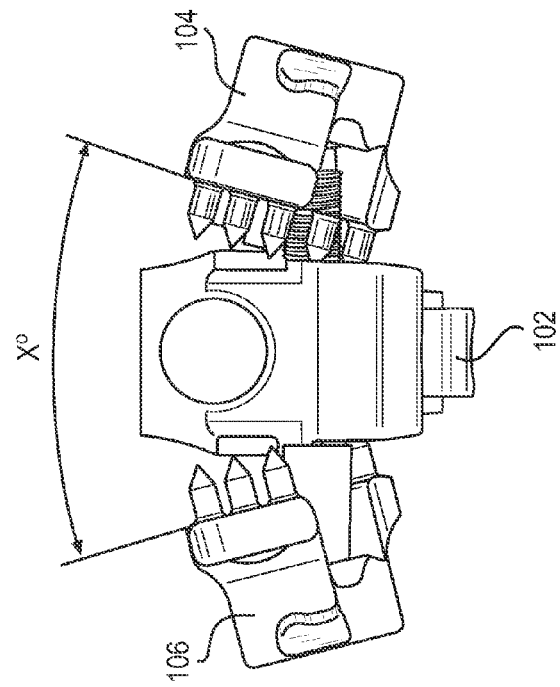
FIG. 11D is a top view of an example spacer assembly having articulated lateral plates.
Figure 11C:
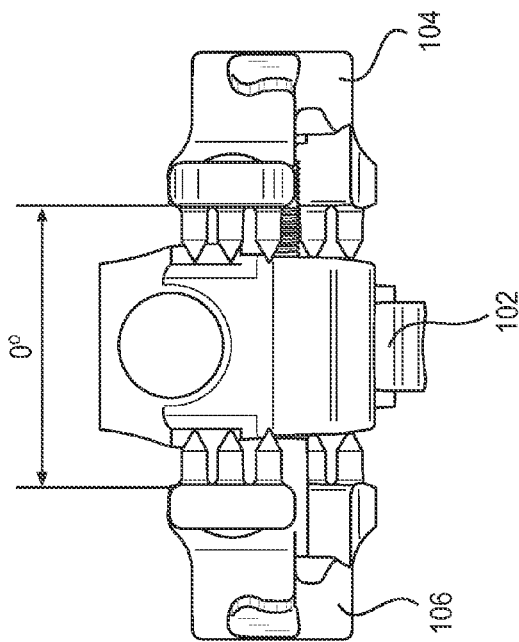
FIG. 11C is a top view of an example spacer assembly having articulated lateral plates.

As outlined above, the locking mechanism 108 can rotate and pivot with respect to the first and second lateral plates 104, 106. In addition to limiting rotational movement of the locking mechanism 108, articulation/pivotal motion between the locking mechanism 108 and the first (and/or second) lateral plate 104 can also be limited. FIGS. 11A-11D provide the spacer assembly 100 at example articulation (pivot) angles. As illustrated in FIGS. 11A and 11B, the lateral plates 104, 106 can articulate in the coronal plane with respect to the spacer body 102 and the locking mechanism 108. The first and second lateral plates 104, 106 can articulate about the heads 144, 146 of the locking mechanism 108. The first and second lateral plates 104, 106 can articulate independently of one another to conform to the bony anatomy of the spinous processes. The first and second lateral plates 104, 106 can articulate in the coronal (FIGS. 11A and 11B) and/or axial planes (FIGS. 11C and 11D). As outlined below, the first and second lateral plates 104, 106 can articulate within a predetermine range of motion to accommodate patient anatomy. For example, in the coronal plane, each of the first and second lateral plates 104, 106 can articulate about −3° to about 3°. In another example, the first and second lateral plates 104, 106 can articulate about −2.5° to about 2.5°. As illustrated in FIG. 11A, the top feet plates 138 of the first and second lateral plates 104, 106 have a negative articulation angle, and the bottom feet plates 138 have a positive articulation angle. That it, the superior foot plates 138 tilted inward and the inferior foot plates 138 are tilted outward. FIG. 11B illustrates the top feet plates 138 having a positive articulation angle and the bottom feet plates 138 having a negative articulation angle. That is, the superior foot plates 138 tilted outward and the inferior foot plates 138 tilted inward.

Likewise, the first and second lateral plates 104, 106 can articulate in the axial plane within a predetermined range of motion to accommodate patient anatomy and permit the force applied by the crimping tool 200 to direct installation of the first and second lateral plates 104, 106. For example, a smaller maxim articulation angle can direct more of the force applied by the crimping tool 200 toward the lateral plates 104, 106 and direct the foot plates 138 for implanting the surface features 140 in the spinous process. For example, FIGS. 11C and 11D illustrate articulation of the first and second lateral plates 104, 106 from 0° (FIG. 11C) to fully articulated position having a total articulation angle represented by X° in FIG. 11D. In an example spacer assembly 100, each of the first and second lateral plates 104, 106 can articulate in the axial plane from about 0° to about 23°, thereby providing a total articulation angle)(X° between the first and second lateral plates 104, 106 of about 45°. In another example, the first and second lateral plates 104, 106 can articulate in the axial plane from about 0° to about 15°, thereby providing a total articulation angle)(X° between the first and second lateral plates 104, 106 of about 30°.

In an example spacer assembly 100, the interface between the locking mechanism 108 and the bores 162, 164 included in the first and second lateral plates 104, 106 can limit the articulating/pivoting motion. As illustrated in FIGS. 6A and 6C, the first lateral plate 104 (and/or the second lateral plate 106) includes a bore 164 for receiving the first locking member 122. Articulating/pivoting motion can be limited by interference between the bore 164 and the outer surface of the first locking member 122 as the first locking member 122 pivots in the lateral and/or vertical directions. That is, the clearance between the bore 164 and the outer surface of the first locking member 122 can define the limit of the articulating/pivoting motion available between the first locking member 122 and the first lateral plate 104. As the elongated body portion 132 of the locking mechanism 108 moves in the lateral or vertical direction, an outer surface of the first locking member 122 (e.g., a surface of the elongated body 132, the neck 148, and/or the head 144) can impact or come into contact with the side wall of the bore 162 thereby preventing further movement in a given direction. The amount of clearance between the bore 162 and the outer surface of the first locking member 122 determines the amount of movement available in a given direction. For example, the greater the clearance the more the first locking member 122 will be able to articulate/pivot in a given direction with respect to the bore 162. The first locking member 122 can be centered within the bore 162 and the clearance between the first locking member 122 and the bore 162 can be uniform around the diameter of the first locking member 122/bore 162. In another example, the first locking member 122 is not centered within the bore 162 and the clearance between bore 162 and the outer surface of the first locking member 122 varies around the diameter of the first locking member 122/bore 162. In another example, the bore 162 has an elliptical, square or any other regular or irregular shape, and the first locking member 122 is not centered within the bore 162.

The spacer assembly 100 can be inserted and/or adjusted on the spinous process using various medical instruments. As illustrated in FIGS. 1 A-C, 2A and 2B, the first and second lateral plates 104, 106 can include indentations sized and configured to mate with various medical instruments. For example, these indentations can serve as an interface for various crimping instruments that are used to fix the first and second lateral plates 104, 106 on/in the spinous processes and embedding the surface features 140 into the spinous process. In another example, the indentations serve as an interface for crimping instruments used to deform the first and second lateral plates 104, 106 to engage the spinous process. In an example spacer assembly 100, the first and second lateral plates 104, 106 include at least one indentation 170 that serves as an interface and attachment point for a crimping tool 200. The first and second lateral plates 104, 106 can also include at least one tip indentation 172 that serves as an interface and attachment point for a tip crimping tool 250. The tip crimping tool 250 can include a plier-type instrument used to adjust the lateral plate position. The tip crimping tool 250 can be designed such that torque applied to the handle of the tool compresses the lateral plates 104, 106 together through a rack and pinion design.

In another example, the spacer assembly 100 can include projections configured to engage various medical instruments. For example, in the example spacer assembly 100 illustrated in FIGS. 12A and 12B, the locking mechanism 108 can include radial projections 1204 extending from the outer surface of each of the first and second locking members 122, 124. The radial projections 1204 can serve as an interface and attachment point for a crimping tool 200 during compression of the first and second lateral plates 104, 106 against the spinous process. By fixing the crimping tool 200 to the locking mechanism 108 at the radial projections 1204, rather than the first and/or second lateral plates 104, 106 during insertion of the spacer assembly 100, the first and second lateral plates 104, 106 can rotate and/or articulate during the insertion and crimping process to accommodate the anatomy of the spinous process. The foot plates 138 of each of the first and second lateral plates 104, 106 can include a single surface feature 140. The surface feature 140 can have a "C" shaped cross-section and be located on each of the foot plates 138 at offset positions. In the example spacer assembly 100 illustrated in FIGS. 10 A-10C, the locking mechanism 108 also includes radial projections 1012 extending from the outer surface of each of the first and second locking members 122, 124. The radial projections 1012 can also serve as an interface and attachment point for a crimping tool 200 during compression of the first and second lateral plates 104, 106 against the spinous process.

Figure 13A:
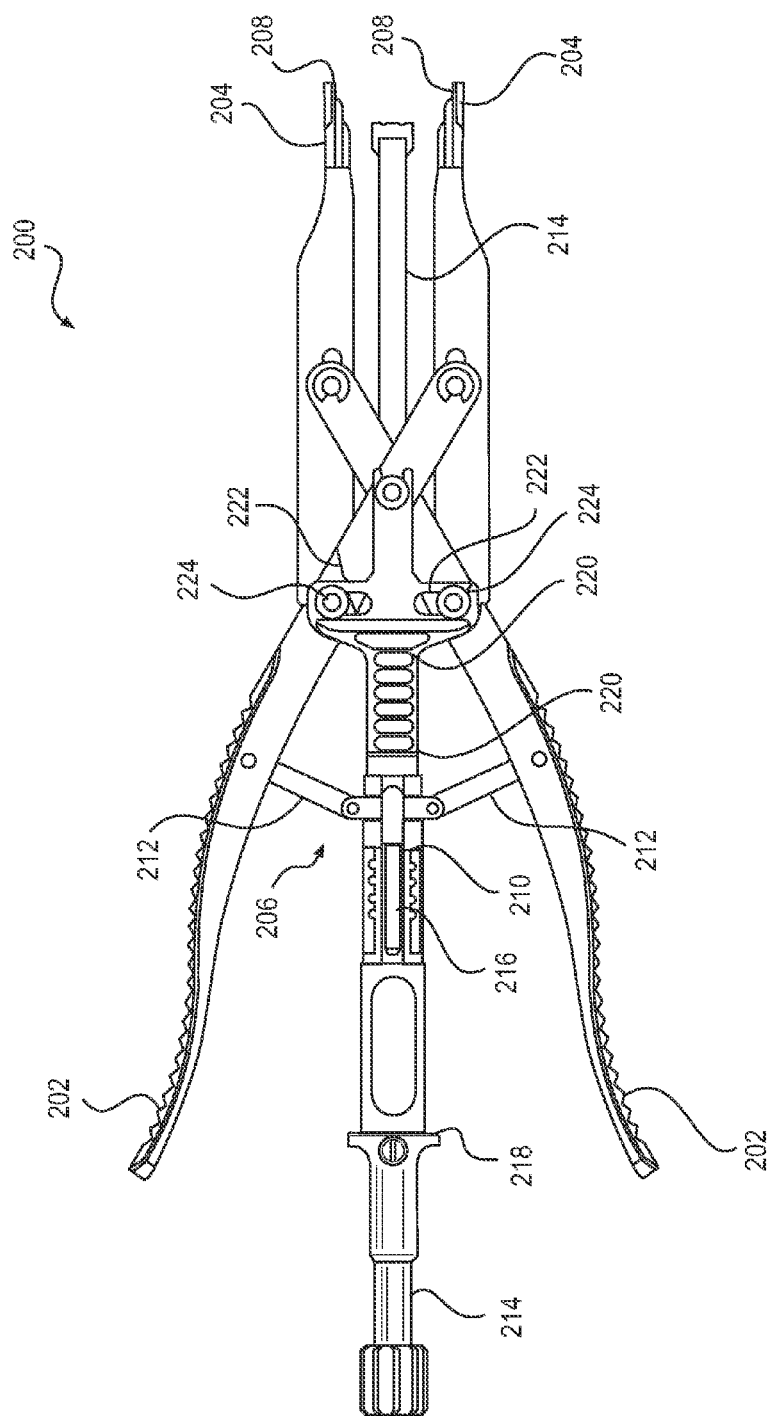
FIG. 13A is a top plan view of an example crimping tool with the handles open.
Figure 17B:
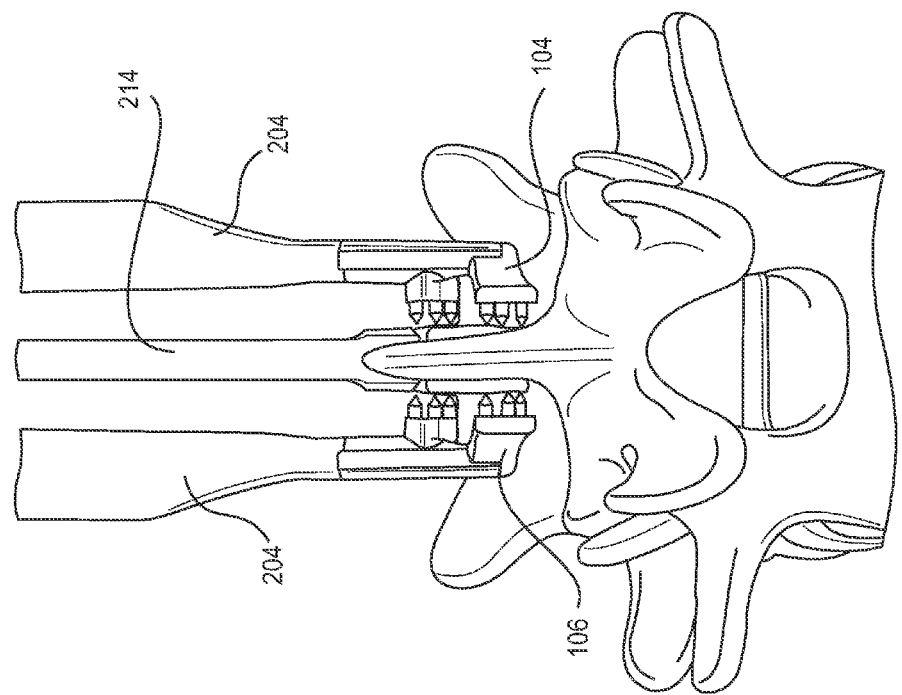
FIG. 17B is a top view of an example spacer assembly being installed between adjacent spinous processes.
Figure 17A:
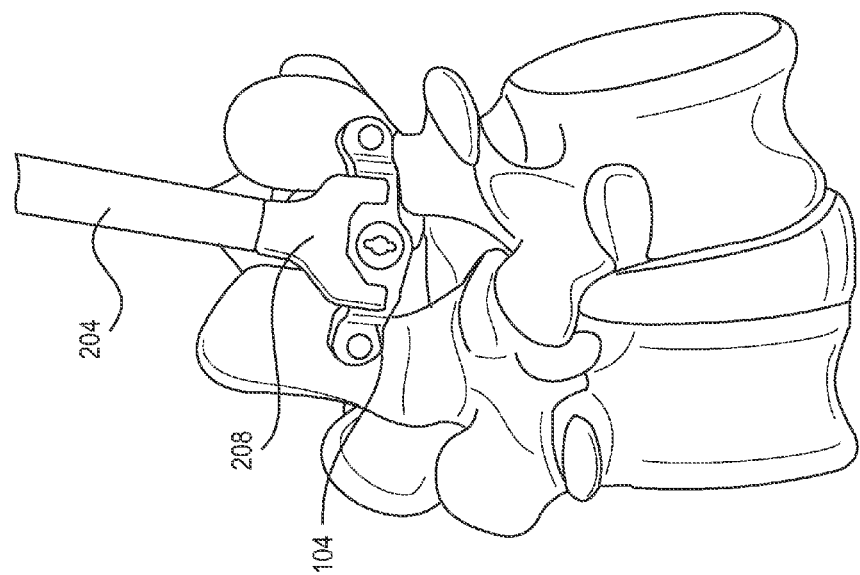
FIG. 17A is a side view of an example spacer assembly being installed between adjacent spinous processes.

FIGS. 13A-C provide various views of an example crimping tool 200 in an open configuration (FIG. 13A) and closed (FIGS. 13B and 13C) configuration. The crimping tool 200 includes a pair of handles 202, a pair of opposing jaws 204, and a linkage mechanism 206. The jaws 204 can include an interface 208 that is sized and configured to releasably mate with the plate indentations 170 and/or tip indentations 172 included on the spacer assembly 100. The interface 208 facilitates insertion and implantation of the spacer assembly 100 in/on the spinous process. The interface 208 can be configured to pivot within a certain range of motion in the frontal plane. For example, the interface 208 can pivot in response to the articulation of the first and second lateral plates 104, 106. For example, the interface 208 can be coupled to the jaws 204 using screws and/or pins that permit a range of rotation of the interface 208 with respect to the jaws 204. The lateral profile of the jaws 204 in an open configuration, as illustrated in FIG. 17B, can be configured such that the width/profile does not exceed the width/profile of the spacer assembly 100. This minimizes the amount of lateral muscle retraction needed to insert the spacer assembly 100 thereby allowing for a quicker recovery time for the patient.

Figures 18A, 18B:
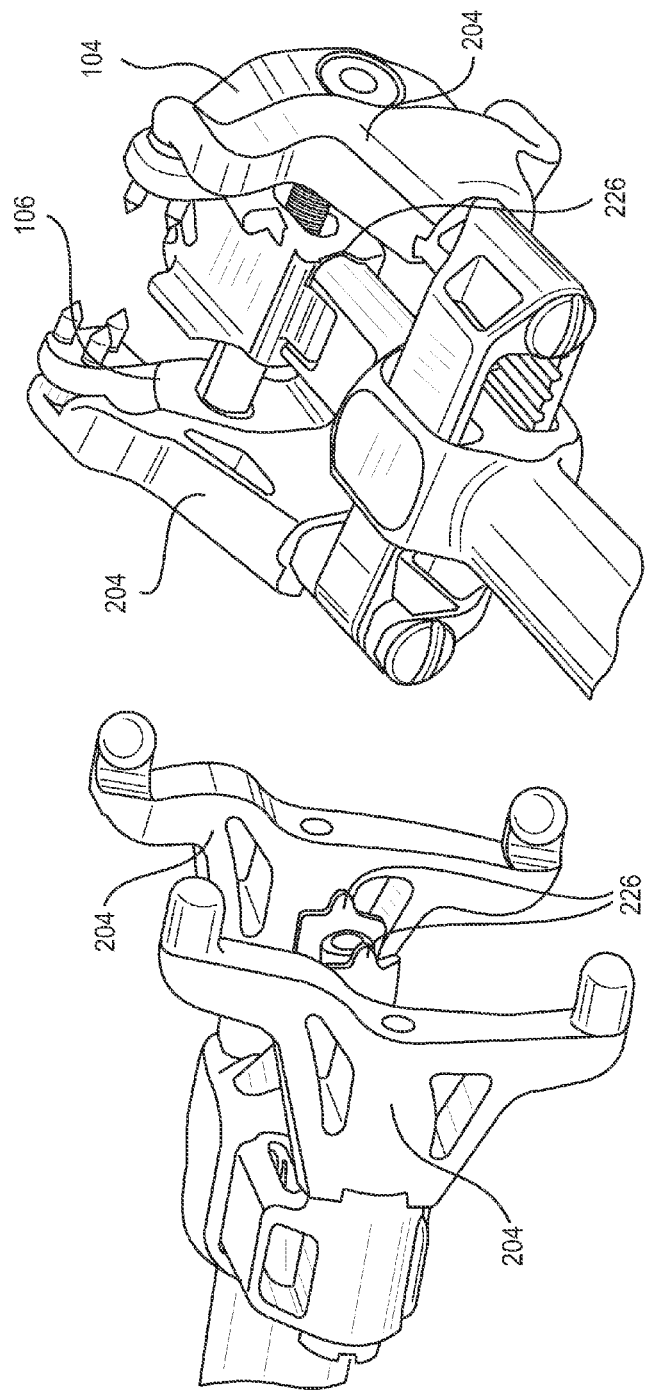
FIG. 18A is a partial perspective view of an example crimping tool.
FIG. 18B is a partial perspective view of an example crimping tool and spacer assembly.
Figure 18C:
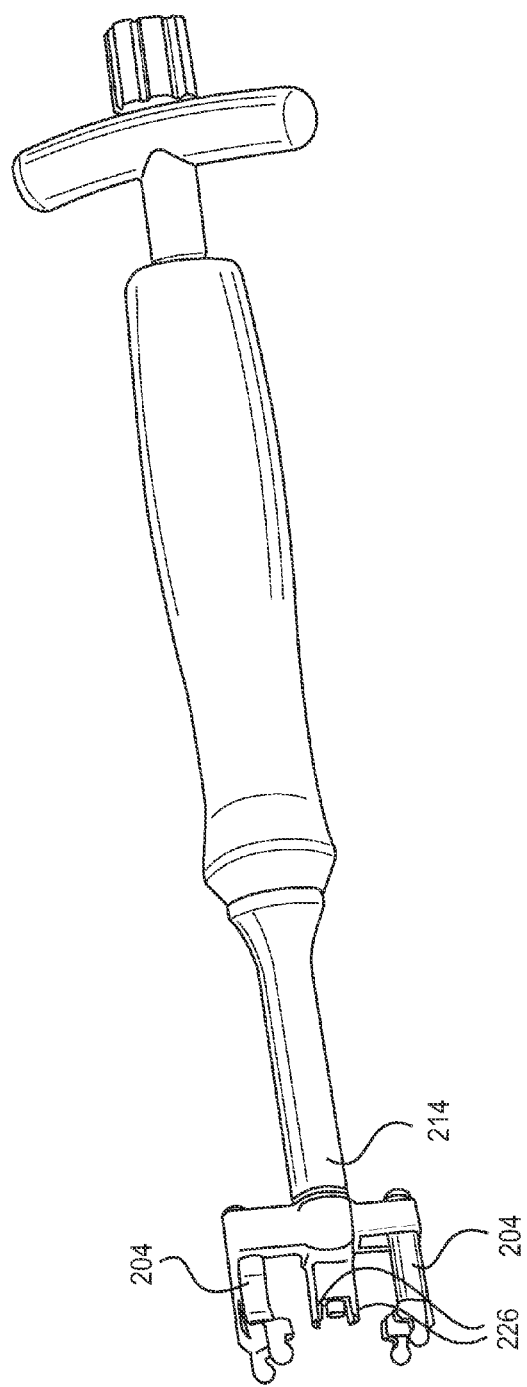
FIG. 18C is a perspective view of an example crimping tool.

In another example spacer assembly illustrated in FIGS. 18A and 18B, the implant holder and crimping features are combined into a single crimping tool 200. In the center shaft 214 includes lateral projections 226 extending from the distal surface of the center shaft 214. The lateral projections 226 interface with the space body 102 of the assembly 100. A cannulated rod (not shown) inside the center shaft 214 engages the threaded bore 126 of the spacer body 102. In another example, a rod (not shown) extends through the center shaft 214. The rod can engage the spacer body 102 and movement of a handle associated with the rod can provide a rack and pinion action for the jaws 204.

The linkage mechanism 206 can translate movement of the handles 202 into corresponding movement of the jaws 204. For example, opening and closing of the handles 202 translates into a corresponding opening and closing of the jaws 204. The linkage mechanism 206 can allow translation of the jaws 204 (opening and closing in a direction perpendicular to the longitudinal axis of the crimping tool 200) but prevent rotation of the jaws 204 relative to each other or the remaining portions of the crimping tool 200.

The handles 202 include a contoured surface and gripping elements to maximize grip through the full range of handle motion. The handles 202 can be connected to the linkage mechanism 206 at the linkage sleeve 210. For example, the crimping tool 200 can include links 212 connecting the handle 202 to a linkage sleeve 210. The linkage sleeve 210 can include a spring loaded sleeve on a center shaft 214 of the crimping tool 200. The spring 216 can push back on the linkage sleeve 210 causing the handles 202 (and jaws 204) to close. As a result, the crimping tool 200 can default to a closed configuration. To open the crimping tool 200, a master sleeve 218 is pushed along the center shaft 214 in a direction towards the jaws 204 compressing the spring 216 within the linkage sleeve 210, directing the links 212 outward and forcing the handles 202 (and jaws 204) into an open configuration. Similarly, any combination of leaf springs, torsion springs, compression and extension springs could be used to bias the handles 202 in an open or closed configuration. In another example spacer assembly 100, the linkage mechanism 206 can include a ratchet assembly including a rack-style structure to control the position of the handles 202 and jaws 204.

The jaws 204 can be locked in the open configuration. For example, the master sleeve 218 can include a locking feature to fix the location of the master sleeve 218 along the center shaft 214 and prevent release of the spring 216 within the linkage sleeve 210. The locking feature can be activated by manipulating the rotational location of the master sleeve 218 about the center shaft. For example, rotating the master sleeve 218 in a clockwise and/or counterclockwise direction a predetermined amount can activate the locking feature. In another example, the locking feature can include a threaded portion used to advance the master sleeve 218 along the center shaft 214. In a further example, the locking feature can include a ball lock/dentent pin combination. Likewise, the jaws 204 of the crimping tool 200 can be release from their locked (open) position by releasing the locking mechanism. By locking the jaws 204 in an open configuration during the insertion process, inadvertent/premature squeezing of the handles 202 can be prevented. For example, during the insertion process, impaction forces used to place the spacer assembly 100 at the desired location can cause the crimping tool 200 to slip in the surgeon's hand, thereby resulting in the inadvertent/premature squeezing on the handles 202. This can be prevented when the handles 202 are locked in the open configuration because only when the surgeon is ready to compress the first and second lateral plates 104, 106 into the spinous processes, he/she can unlock the jaws 204 from their open configuration. Moreover, during the crimping process, when the handles 202 are unlocked from the open configuration, the spring 216 force keeps the jaws 204 closed and fully engaged with the first and second lateral plates 104, 106 at all times. If the surgeon has to adjust his/her grip on the handles 202, he/she can do so without "losing" the previous jaw 204 position and additional crimping (compressive) force can then be applied (if desired).

Figure 20:
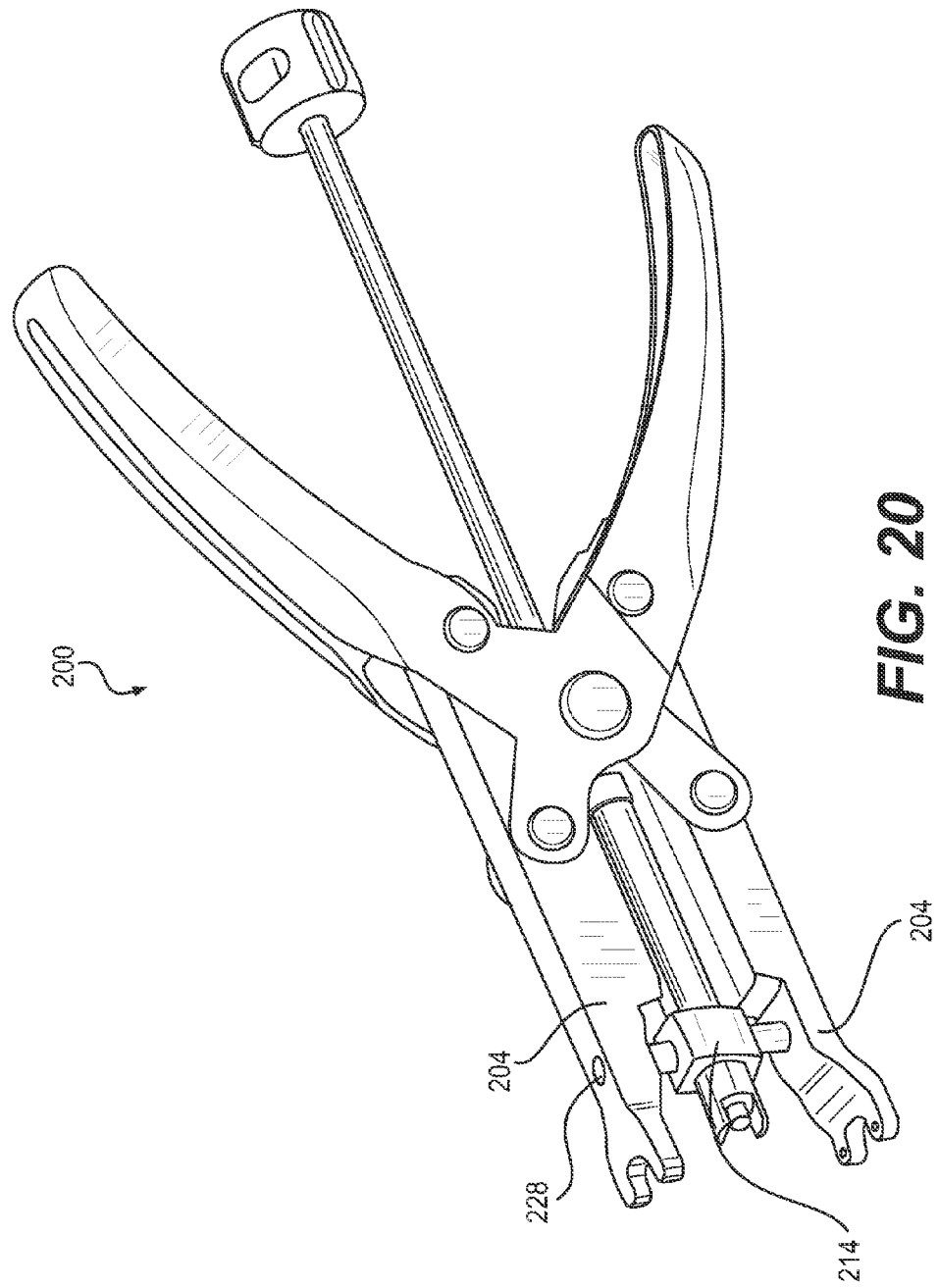
FIG. 20 is a perspective view of an example crimping tool.

The crimping tool 200 can include a central base 220 that connects the center shaft 214 with the linkage mechanism 206. The central base 220 can include slots 222 that engage a corresponding projection 224 from the handle 202. The slots 222 can be perpendicular to the longitudinal axis of the crimping tool 200. The slots 222 fix the location of the center shaft 214 such that the center shaft 214 remains mid-way between the jaws 204 through the range of handle positions. In another example spacer assembly illustrated in FIG. 20, the crimping tool 200 includes a pin 228 extending perpendicular to the longitudinal axis of the crimping tool 200. The pin 228 connects the jaws 204 and the center shaft 214 such that the center shaft 214 remains mid-way between the jaws 204 through the range of handle positions.

The center shaft 214 can include a central channel passing therethrough. The central channel can be sized and configured to receive a cannulated rod 230. An example cannulated rod 230 is illustrated in FIGS. 14A-C. The cannulated rod 230 can also include a central channel passing therethrough. The cannulated rod 230 can include a threaded portion 232 located on the distal end and a knob 234 located at the proximal end. The threaded portion 232 can be configured to couple with the spacer body 102 and can extend along the entire length of the cannulated rod 230 or along a portion of the length of the cannulated rod 230.

Figure 19:
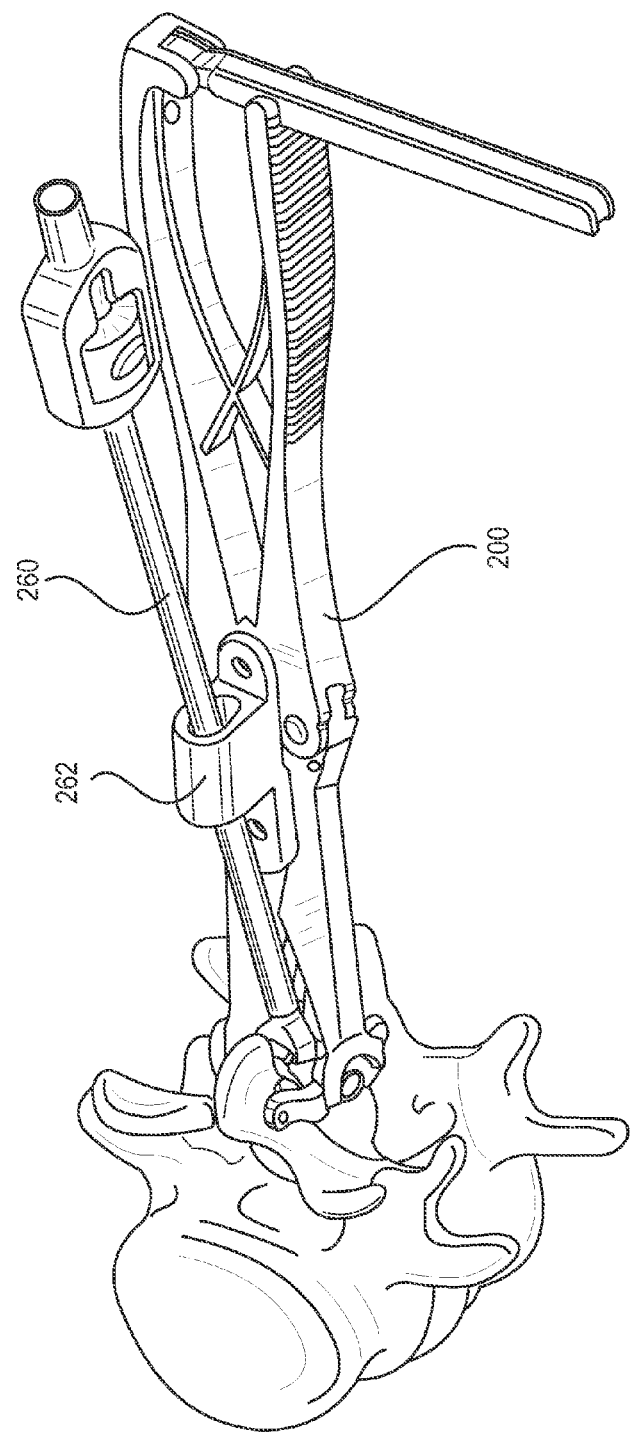
FIG. 19 is a perspective view of an example implant holder and crimping tool.

In another example spacer assembly illustrated in FIG. 19, an implant holder 260 can be used couple the spacer body 102 to the crimping tool 200. The implant holder 260 coupled to the spacer body 102 can be fixed to the crimping tool 200 at an attachment point 262. As provided in FIG. 19, movement of the implant holder 260 along the longitudinal axis of the crimping tool 200 can be fixed or unrestricted at the attachment point 262.

Figures 15A, 15B:
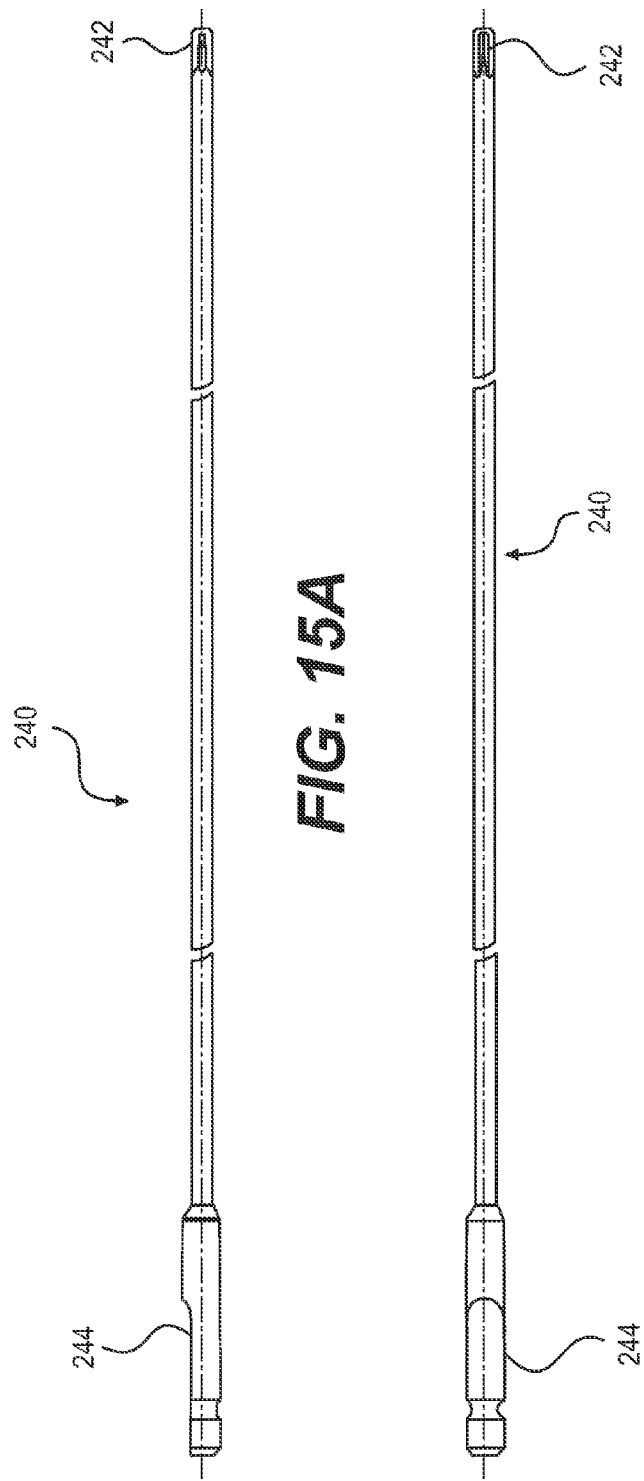
FIG. 15A is a side view of an example driver.
FIG. 15B is a plan view of an example driver.

The central channel of the cannulated rod 230 can be sized and configured to receive various medical instruments including, for example, a driver 240. An example driver 240 is illustrated in FIGS. 15A and 15B. The distal end of the driver 240 can include a driver head 242 sized and configured to mate with a corresponding socket or recess in set screw 128 to fix the position of the locking mechanism 108. The driver head 242 can have a various configurations including, for example, slotted (flathead), cross slot (Phillips), square, torx, hexagon, and/or any other known configuration known in the art. The proximal end of the driver 240 can include a connector 244 for coupling the driver 240 to a handle or other rotation mechanism for rotating the driver 240.

In an alternate example, the crimping tool 200 can be configured to distract the spacer assembly 100 from the spinous process. For example, bias and/or direction of the linkage mechanism 206 can be reversed to provide a tensile stress to the first and second lateral plates 104, 106 (rather than the compressive force applied by the initial configuration). A distractive crimping tool 200 can be used to distract pedicle screw constructs. Similarly, the distractive crimping tool 200 could be configured to hold the rod portion of the pedicle screw construct while compressing or distracting the screw along the rod. The distractive crimping tool 200 could be used to open the disc and/or interspinous space and distract it to the desired vertebral height.

Figure 16A:
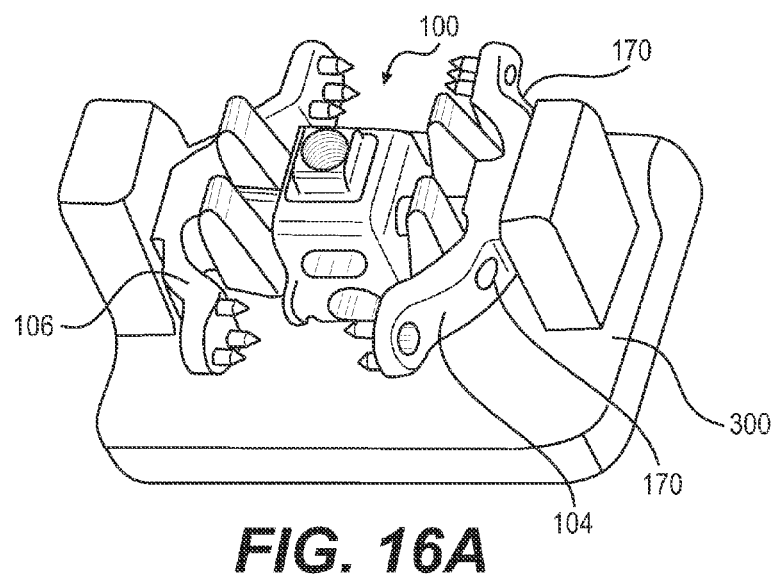
FIG. 16A is a perspective view of an example spacer assembly and loading station.
Figure 16B:
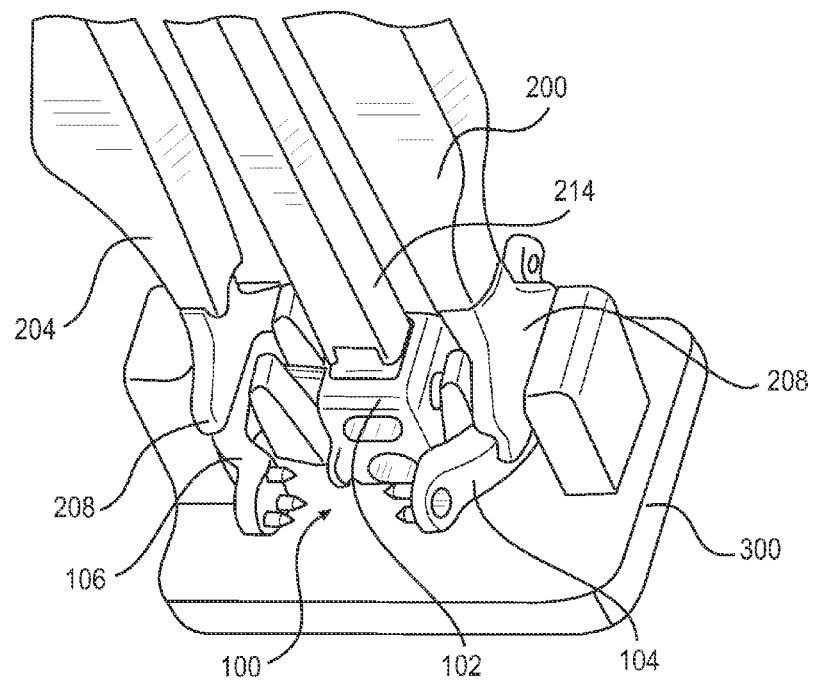
FIG. 16B is a partial perspective view of an example spacer assembly, loading station, and tool.

To load the spacer assembly 100 on to crimping tool 200, the handles 202 can be locked in an open configuration. The spacer assembly 100 is configured such that the first and second lateral plates 104, 106 are at a distance apart corresponding with the distance apart of the jaws 204. The spacer assembly 100 can be placed in a loading station 300 as illustrated in FIG. 16A. In another example, the spacer assembly 100 need not be placed in a loading station 300 during fixation to the crimping tool 200. The interface 208 on the jaws 204 engages the plate indentations 170 on the first and second lateral plates 104, 106 as illustrated in FIG. 16B. The cannulated rod 230, located within the central channel of the center shaft 214, can extend through the central channel and engage the spacer body 102. For example, the threaded portion 232 can be releasably mated with a corresponding threaded bore (e.g., threaded bore 126) included on the spacer body 102. The cannulated rod 230 can be threaded on to the spacer body 102 such that the crimping tool 200 is securely attached to the spacer body 102. The cannulated rod 230 can be threaded on to the spacer body 102 such that the outer surface of the spacer body 102 is against the center shaft 214. In another example, the cannulated rod 230 can include a non-threaded connection structure. For example, the cannulated rod 230 can include a press fit, snap fit, other means of mechanical connection for coupling the cannulated rod 230 to the spacer body 102.

Figure 16C:
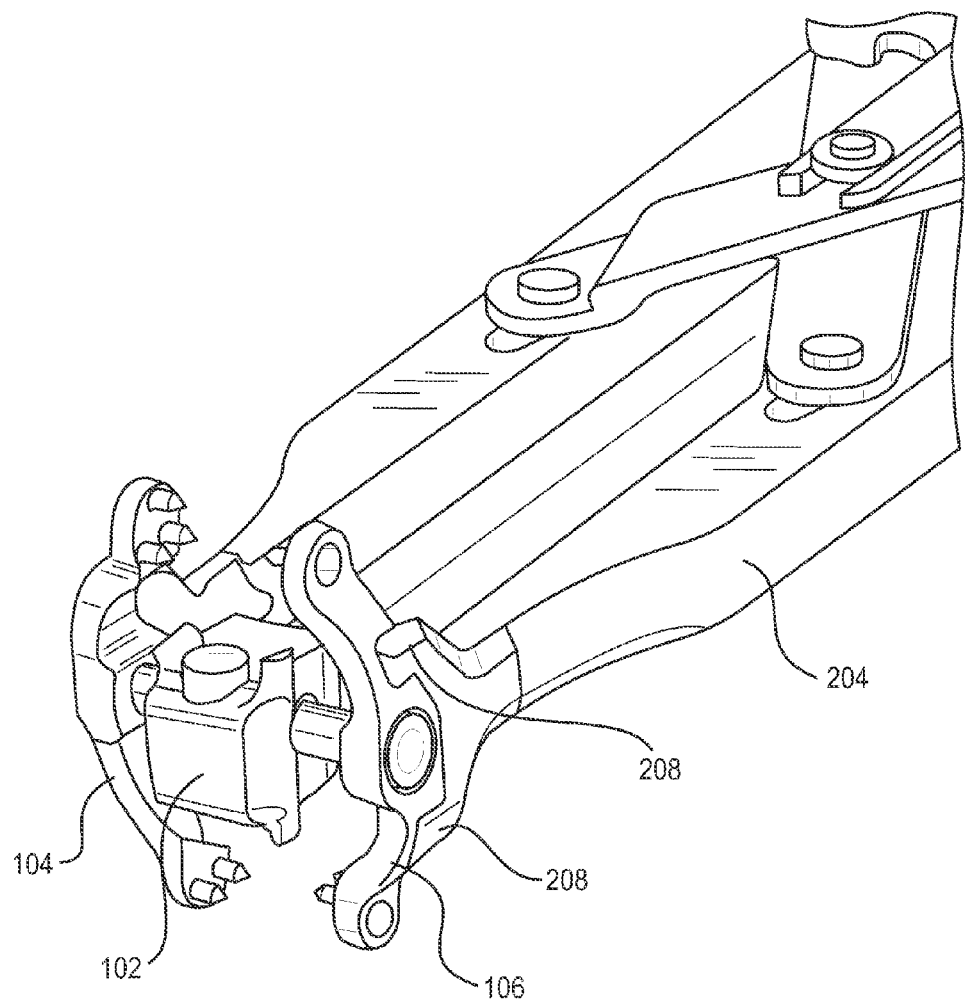
FIG. 16C is a partial perspective view of an example spacer assembly and tool.

If a loading station 300 is used, after the spacer assembly 100 is loaded on to the crimping tool 200, the spacer assembly 100 can be removed from the loading station 300 (or other packaging) as illustrated in FIG. 16C.

Figure 17D:
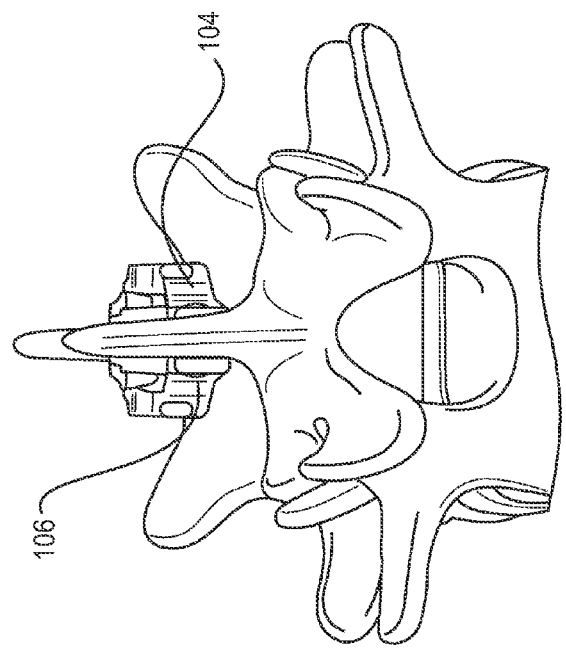
FIG. 17D is a top view of an example spacer assembly installed between adjacent spinous processes.
Figure 17C:
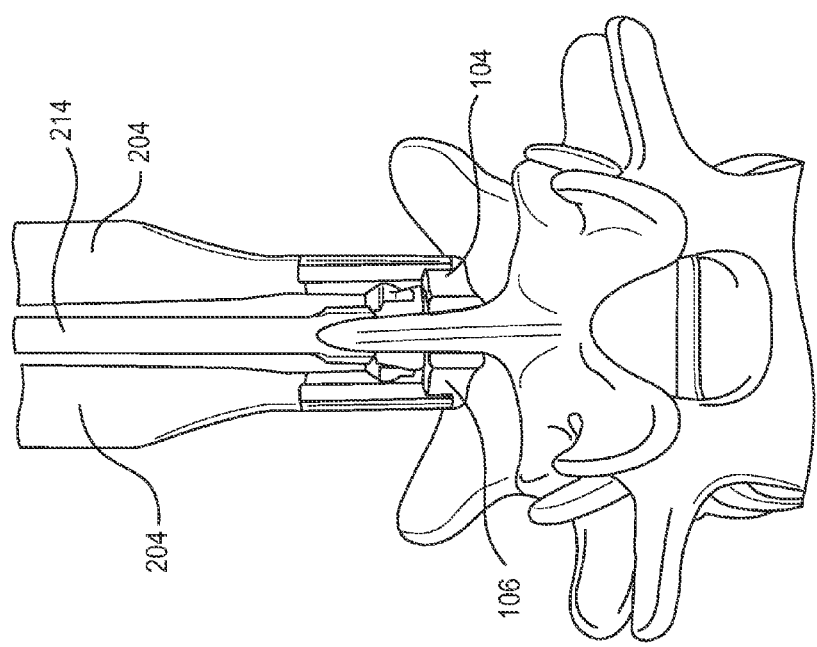
FIG. 17C is a top view of an example spacer assembly installed between adjacent spinous processes and an example crimping tool.

Once removed from the loading station 300 and/or any packaging material, the spacer assembly 100 is ready for insertion in/on the spinous process. If desired, the cavity 114 in the spacer body 102 can be filled with graft material prior to installation of the spacer assembly 100. As illustrated in FIGS. 17 A-17D, the spacer assembly 100 can then be inserted into the patient such that the jaws 204 of the crimping tool 200 straddle the spinous processes of the spine with the spacer assembly 100 located between the jaws 204. Once the spacer assembly 100 is located at the desired position, the handles 202 can be released from the open position (unlocked). The handles 202 can be compressed such that the jaws 204 and their associated lateral plates 104, 106 are compressed against the spinous processes as illustrated in FIG. 17C. Once the surface features 140 (e.g., teeth) are embedded into the bone (lamina) of the spinous process, a driver 240 can be inserted through the central channel of the cannulated rod 230 and mated with the spacer body 102. The driver 240 can engage the set screw 128 located in the spacer body 102 to thread the set screw 128 into the threaded bore 126 and engage the locking mechanism 108. The set screw 128 is advanced until the location of the locking mechanism 108 is fixed with respect to the spacer body 102.

After the set screw 128 is tightened to a satisfactory level and the location of the locking mechanism is fixed, the driver 240 can be disengaged from the spacer body 102 and removed from the crimping tool 200. Likewise, the cannulated rod 230 can be disengaged from the spacer body 102 (and removed from the crimping tool 200 if desired).

The handles 202 can then be opened to release the jaws 204 from the plate indentations 170. The crimping tool 200 can then be disengaged from the spacer assembly 100 leaving it fixated to the spinous processes, as illustrated in FIG. 17D. To remove or relocate the spacer assembly 100, the process is completed in reverse. After the set screw 128 is loosened, the plates can be pried apart/from the surface of the spinous process as removed or relocated as desired.

One or more components of the spacer assembly 100 and crimping tool 200 may be made from any biocompatible material known including, for example, metals such as titanium, titanium alloys, stainless steel and cobalt chromium. Other materials include, for example, composites, polymers, ceramics, bone (allograft) and any other materials suitable for the spacer assembly 100 crimping tool 200. In one example, the spacer assembly 100 crimping tool 200 can be constructed from a radiopaque material including, for example, stainless steel such as 17-4PH stainless steel. Likewise, one or more components of the spacer assembly 100 crimping tool 200 can be constructed from a radiolucent material to enhance visibility of the assembly during radiographic imaging. For example, it is contemplated that the jaws 204, interface 208, and cannulated rod 230 (in particular the threaded portion 232 of the cannulated rod 230) be made of a radiolucent material. Example radiolucent materials can include "life science" grade PEEK (Ketron 450G PEEK). Life science grade PEEK can improve wear and abrasion characteristics as well as provide high yield strength.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. An interspinous spacer assembly for insertion into an interspinous space between spinous processes of adjacent vertebral bodies, the assembly comprising:

a spacer body sized and configured for insertion between adjacent spinous processes, the spacer body including a channel extending therethrough;

a first lateral plate and a second lateral plate for coupling the spacer assembly to the spinous processes; and a locking mechanism extending through the channel in the spacer body and coupling the first and second lateral plates to the spacer body, the locking mechanism including a first locking member and a second locking member configured to move relative to each other in a longitudinal direction of the locking mechanism, the second locking member having hollow cylindrical body for receiving a body of the first locking member, wherein the channel included in the spacer body includes a protrusion extending from a surface of the channel, the protrusion sized and configured to mate with a corresponding recess provided in the first locking member, wherein the second locking member includes an opening along a length of the hollow cylindrical body such that the recess provided in the first locking member is accessible via the opening.

2. The interspinous spacer assembly of claim 1, further including a first and second locking cap for rotateably engaging the first and second locking members within the first and second lateral plates, respectively.

3. The interspinous spacer assembly of claim 1, further including a set screw provided within a corresponding opening located on a posterior surface of the spacer body, the set screw fixing the location of the locking mechanism.

4. The interspinous spacer assembly of claim 1,
wherein the protrusion included in the channel of the spacer body controls rotation of the locking mechanism within the channel within a predetermined range.

5. The interspinous spacer assembly of claim 1, wherein the spacer body includes a cavity sized and configured to receive graft material.

6. The interspinous spacer assembly of claim 5, wherein the cavity is located on an anterior portion running between a superior surface and an inferior surface of the spacer body.

7. The interspinous spacer assembly of claim 1, wherein the spacer body includes a cranial surface for contacting an inferior surface of the spinous process of the superior vertebral body.

8. The interspinous spacer assembly of claim 1, wherein the spacer body includes a caudal surface for contacting a superior surface of the spinous process of the inferior vertebral body.

9. The interspinous spacer assembly of claim 1, wherein the body of the first locking member includes an engagement feature sized and configured to releasably engage with a corresponding engagement feature on an interior surface of the hollow cylindrical body of the second locking member,
wherein the engagement feature includes a surface feature extending from an outer surface of the body of the first locking member,
wherein the corresponding engagement feature includes a corresponding surface feature on the interior surface of the hollow cylindrical body of the second locking member.

10. The interspinous spacer assembly of claim 9, wherein the surface feature of the first locking member is asymmetrical with respect to the corresponding surface feature of the second locking member.

11. The interspinous spacer assembly of claim 1, wherein the first locking member includes a head and a neck located between the body of the first locking member and the head,
wherein the second locking member includes a head and a neck located between the hollow cylindrical body and the head,
wherein the heads of each of the first and second locking members include a curved surface sized and configured to correspond to a curved cavity included in each of the first and second lateral plates.

12. The interspinous spacer assembly of claim 11, wherein the heads of each of the first and second locking members include a head engagement feature sized and configured to mate with a corresponding plate engagement features on the first and second lateral plates,
wherein the interaction between the head engagement feature and the plate engagement feature limits rotation of the first and second locking members within the first and second lateral plates within a predetermined range.

13. The interspinous spacer assembly of claim 12, wherein the plate engagement feature includes a key on a surface of the curved cavity of each of the first and second lateral plates, and the head engagement feature includes a corresponding recess in the curved surfaces of each of the first and second locking members.

14. The interspinous spacer assembly of claim 1, wherein the hollow cylindrical body defines a C-shaped cylindrical sleeve.

15. The interspinous spacer assembly of claim 1, wherein the first and second lateral plates include a foot plate for contacting the outer surface of the spinous processes.

16. The interspinous spacer assembly of claim 15, wherein the foot plate is angled in a frontal plane.

17. The interspinous spacer assembly of claim 15, wherein the foot plate includes a surface feature that is configured to extend into the spinous processes for coupling the spacer assembly to the spinous processes.

18. The interspinous spacer assembly of claim 1, wherein the first and second lateral plates each include at least one indentation for mating with a medical tool.

19. The interspinous spacer assembly of claim 1, wherein the spacer assembly is constructed from a radiopaque material.

20. The interspinous spacer assembly of claim 1, wherein the spacer body is made of radiolucent material.

* * * * *